(12) United States Patent
Jiao et al.

(10) Patent No.: US 11,529,384 B2
(45) Date of Patent: *Dec. 20, 2022

(54) NATURAL PRESERVATIVES AND ANTIMICROBIAL AGENTS, INCLUDING COMPOSITIONS THEREOF

(71) Applicant: Unigen, Inc., Tacoma, WA (US)

(72) Inventors: Ping Jiao, Newcastle, WA (US); Mi sun Oh, Tacoma, WA (US); Mei Feng Hong, Lacey, WA (US); Qi Jia, Olympia, WA (US)

(73) Assignee: Unigen, Inc., Tacoma, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/026,736

(22) Filed: Sep. 21, 2020

(65) Prior Publication Data

US 2021/0000902 A1   Jan. 7, 2021

Related U.S. Application Data

(63) Continuation-in-part of application No. 15/345,006, filed on Nov. 7, 2016, now Pat. No. 10,780,173.

(60) Provisional application No. 62/252,987, filed on Nov. 9, 2015.

(51) Int. Cl.

| *A61K 36/575* | (2006.01) |
|---|---|
| *A61K 36/48* | (2006.01) |
| *A61K 45/06* | (2006.01) |
| *A61K 8/9789* | (2017.01) |
| *A23L 33/105* | (2016.01) |
| *A61Q 5/02* | (2006.01) |
| *A61Q 19/00* | (2006.01) |
| *A61Q 11/00* | (2006.01) |

(52) U.S. Cl.
CPC .......... *A61K 36/575* (2013.01); *A23L 33/105* (2016.08); *A61K 8/9789* (2017.08); *A61K 36/48* (2013.01); *A61K 45/06* (2013.01); *A61Q 5/02* (2013.01); *A61Q 11/00* (2013.01); *A61Q 19/00* (2013.01); *A23V 2002/00* (2013.01)

(58) Field of Classification Search
CPC .... A61K 36/575; A61K 8/9789; A61K 36/48; A61K 45/06; A23L 33/105; A61Q 5/02; A61Q 11/00; A61Q 19/00; A23V 2002/00
See application file for complete search history.

(56) References Cited

U.S. PATENT DOCUMENTS

2007/0134168 A1* 6/2007 Dodds ................... A23L 33/105
424/48

OTHER PUBLICATIONS

P. Praveen, et al., Journal of Pharmacy Research 2011, 4(3), 832-835. (Year: 2011).*
W. Mar, et al., Journal of Natural Products, vol. 54, No. 6, pp. 1531-1542 (1991) (Year: 1991).*
Fact Sheet for Magnolia extract from O'Laughlin Industries, downloaded Oct. 29, 2017 from http://www.olaughlinco.com/products/detail/105. (Year: 2017).*
V.K. Bajpai, A. Rahman, N.T. Dung, M.K. Huh, and S.C. Kang, J. Food Sci. 73(6) 2008, pp. M314-M320. (Year: 2008).*
N.A. Khatune, et al. Fitoterapia 2004, 228-230 (Year: 2004).*
Wikipedia entry for Calcium propanoate (Downloaded from https://web.archive.org/web/20100716184539/https://en.wikipedia.org/wiki/Calcium_propanoate on Oct. 28, 2017. Wikipedia entry from Wayback Machine dated Jul. 16, 2010) (Year: 2010).*
Google_search_12-15-21_albizzia (Year: 2021).*

* cited by examiner

*Primary Examiner* — Michael P Cohen
(74) *Attorney, Agent, or Firm* — Sandra Poteat Thompson; Finlayson Toffer

(57) ABSTRACT

Compositions are disclosed herein that comprise a mixture of at least one *Albizia* extract and a *Magnolia* extract. In some embodiments, the composition comprises a mixture of at least one *Albizia* extract enriched for one or more macrocyclic alkaloids and at least one *Magnolia* extract enrich for one or more lignans.

19 Claims, 3 Drawing Sheets

NATURAL PRESERVATIVES AND ANTIMICROBIAL AGENTS, INCLUDING COMPOSITIONS THEREOF

This United States Continuation Utility Application claims priority to United States Utility application Ser. No. 15/345,006, which claims priority to United States Provisional Patent Application Ser. No. 62/252,987 filed on Nov. 9, 2015 and entitled "Natural Preservatives and Antimicrobial Agents", which are commonly-owned and incorporated herein by reference in their entirety.

FIELD OF THE SUBJECT MATTER

The field of the subject matter relates to compositions that can act as preservatives, antimicrobial agents, or a combination thereof and related methods. Contemplated embodiments are directed to preservatives derived from extracts that are derived from *Albizia amara* seeds and *Magnolia officinalis* barks, which can be used to preserve food, cosmetics, nutraceuticals, oral hygiene products, and pharmaceuticals.

BACKGROUND

A preservative is a substance that is added to products, such as foods, pharmaceuticals, cosmetics, biological samples, etc. to prevent decomposition by microbial growth or by undesirable chemical changes. Anti-microbial preservatives prevent the degradation by bacteria, and inhibit the growth of bacteria, fungi and other microorganisms to keep the product quality and extend the shelf life. A preservative can be used by itself or it can be combined with other physical techniques for preservation including dehydration, UV-C radiation, freeze-drying, refrigeration, etc. Anti-oxidant preservatives are commonly used in the food industry, especially the food with a high fat content. Common anti-oxidants include phenol derivatives BHT (butylated hydroxy toluene) and BHA (butylated hydroxyl anisole). Other preservatives include formaldehyde, glutaraldehyde, ethanol and methylchloroisothiazolinone.

Chemical preservatives and physical preservation are usually combined. Common anti-microbial preservatives include sodium nitrate, sodium nitrite, sulfites (sulfur dioxide, sodium bisulfite, and potassium hydrogen sulfite), benzoic acid/sodium benzoate, sorbic acid/sodium sorbate, propionic acid/calcium propionate/sodium propionate, and disodium EDTA targeting on different products. The efficacy, safety and toxicity of many synthetic preservatives are under the scrutiny among academics and regulation agencies because of the adverse reports and concerns from customers, for instance paraben and its analogues, which have been banned in Europe and some Asian countries as well. Natural preservatives are considered safer and more environmentally-friendly alternatives for microbial infection with a broad range of structurally diversified bioactive compounds such as alkaloids, flavonoids, aromatic terpenoids and saponins.

Natural substances such as salt, sugar, vinegar, tea extracts, herb essential oils and organic acids are well accepted as traditional preservatives. For example, citric acid and ascorbic acids from lemon or other citrus juices are commonly used as anti-browning and anti-oxidant in the fruit and juice industry to improve the food quality. However, the current natural preservatives can be expensive or have less potent efficacy, which limits their broader use in food, cosmetics and other biological products industry, compared to the synthetic preservatives, especially the antimicrobial preservatives. Efficient, targeted and appropriate preservatives are critical to extend product shelf life, keep product quality, benefit in many aspects in the whole process and transportation to improve the product safety. Therefore, the idea of discovering and utilizing a special natural composition with potent antimicrobial activity against broad spectrum of microorganisms is practical and appealing.

Thus, there is a need for alternative natural preservatives and antimicrobial agents. To develop natural preservatives, a high-throughput anti-*E. coli* assay was carried out to screen a plant library of over 10,216 organic extracts (OE) and aqueous extracts (AE), which are generated from medicinal plants collected from all over the world, *Albizia amara* seeds extract was identified as the best lead exhibiting potent anti-Gram negative inhibition with a MIC value of 40 ug/mL. Bioassay-guided isolation and identification confirmed the active components are budmunchimaine C, as shown in FIG. 1, and its analogues.

*Albizia* is a genus of about over 150 species distributed mostly in subtropical and tropical areas in Asia, Africa, Madagascar, America and Australia, but mostly in the old world tropics. Many species has been used as folk medicines in India and South Africa countries for cold, diarrhea, headache, intestinal ailments, stomach cancer, sore throat and stomachache. For example the stem bark of *A. schimperiana* is used indigenously for treating bacterial and parasitic infections, and more commonly against fever and in pain relief.

Modern studies of these plants showed antimicrobial, antiparasitic, antitrypanosomal and mosquito larvicidal activities. Further investigation of these *Albizia* plants leads to the discovery of a unique class of macrocyclic alkaloids, represented by budmunchiamines A-I and other analogues (Dixit 1995; Assis 1999; Misra, 1995; Ovenden 2002; Samoylenko 2009). This characteristic type of macrocyclic alkaloids have been reported from seeds of *Albizzia amara, Albizzia lebbek*, stem barks or barks of *Albizzia gummifera, Albizzia schimperana, Albizia saman/Samanea saman, Albizia schimperiana, Albizia adinocephala* leaves of *Albizzia inopinata, Samanea saman(Pithecolobium saman=Albizzia saman)* with a variety of anti-microbial, anti-parasitic and anticancer activities (Samoylenko 2009; Geyid 2005; Thippeswamy 2015; Mar 1991; Pezzutoa 1992).

*Magnolia officinalis*, commonly known as "houpu" in Chinese, is one of the popular components of traditional Chinese medicine having a very wide range of applications is a species of *Magnolia* native in China, mainly growing in Sichuan and Hubei province. Houpu refers to its thick bark, which could be stripped from the stems, branches, and roots. The traditional indications are to treat wind stroke, cold damage, headaches, fight qi and blood impediment. *Magnolia* bark has been used to treat menstrual cramps, abdominal pain, abdominal bloating and gas, nausea, and indigestion. The bark is also an ingredient in formulas used for treating coughs and asthma. Many of the formulations with *Magnolia* bark are used in treating lung diseases such as including cough and asthma or intestinal infections and spasms, relieving abdominal swelling of various causes and edema.

Modern researches discovered potent antimicrobial and antifungal activity of this herb medicine against a variety of microorganism, and bisphenolic lignans are identified as the major active components responsible the antimicrobial efficacy. Magnolol and honokiol, as shown in FIG. 2, are two main polyphenol compounds found in the *magnolia* barks and have been reported with various pharmacological activities and functions such as antioxidant, anti-inflammatory, and antitumor (Park 2004). The anticancer studies of honokiol have been extended to several different solid tumor types such as breast, prostate, gastric, and ovarian cancer, with potential to enhance current anticancer regimens (Fried 2009). Honokiol also reduce inflammation and oxidative stress, providing beneficial effects in neurological protection, and glucose regulation with great potential as therapeutic agents for inflammatory disease. In particular, magnolol and honokiol have been known exhibiting potent antimicrobial activity against Gram-positive and Gram-negative bacteria as well as fungi such as *Propionibacterium* sp. and *S. aureus* showing its potential as antimicrobial agents effective against more infectious resistant microorganisms (Ho 2001; Bang 2000; Kim 2015). The content of honokiol and magnolol could be varied from 1-99% in the commercialized *magnolia* bark extracts.

There are a number of references that help provide context as to why some of these components may be considered important. U.S. Pat. No. 8,329,095 discloses a preservative composition for cosmetic formulations comprising thymol, monolaurin and magnolol obtained from supercritical fluid extracts of *Magnolia officinalis*. U.S. Pat. No. 7,592,025 discloses a vehicle and a method for oral care that includes *Magnolia* Bark Extract in combination with a surface-active agent.

CN 101516364 discloses compositions comprising hydroxytyrosol alcohol and/or oleuropein and at least one additional component selected from the group of the additional components such ligustilide oleuropein aglycone, Magnolol, and Park phenol, genistein, resveratrol, EGCG, *Magnolia* Bark Extract, cashew fruit extract and *Glycyrrhiza foetida* group, contemplated embodiments also relate to the use as a pharmaceutical composition, especially as for the treatment of disorders the treatment or prevention of inflammatory medicine.

CN 1103756 discloses a natural antiseptic agent is made up by mixing 90-99.7% of the extractive powder of bark of official *magnolia* and the rest, the extractive powder of Chinese rhubarb.

CN 100544597 discloses a Chinese herbal preservatives of *Magnolia, Clematis, Humulus, rugosa* as raw materials, based on the different characteristics of each flavor of Chinese herbal medicine.

CN 103416480 discloses a method for a plant source of complex Orange preservatives, plant extracts, food preservatives, stabilizers and acidity regulating agents composite material. The main technical features: the main ingredient containing preservative *Magnolia* extract 10-15%, 20-30% clove extract, potassium sorbate 10-20%, 10-20% propyl paraben, 2-5% citric acid, 1-5% stabilizer traits as a tan emulsion.

WO 2006069209 discloses an efficacious antibacterial and anti-inflammatory oral composition is provided having an active ingredient combination comprising one or more active compounds from an extract of *magnolia* and an extract of hops.

WO 2014131191 discloses a composition comprising an antimicrobial active comprising honokiol and/or magnolol and a carboxylic acid. Also provided are methods of use thereof. None of these references, however, address the need in the art for a composition that acts as a preservative, antimicrobial agent or a combination thereof.

SUMMARY OF THE DISCLOSURE

Compositions are disclosed herein that comprise a mixture of at least one *Albizia* extract and a *Magnolia* extract.

In some embodiments, the composition comprises a mixture of at least one *Albizia* extract enriched for one or more macrocyclic alkaloids and at least one *Magnolia* extract enrich for one or more lignans.

DETAILED DESCRIPTION

Figure 1:
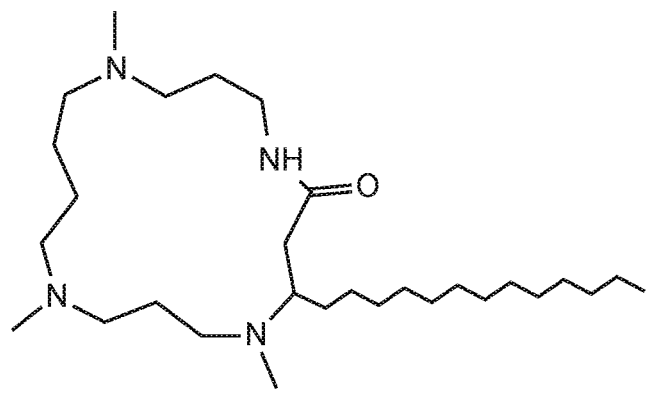
FIG. 1. Chemical structure of budmunchiamine C
FIG. 2. Chemical structures of magnolol and honokiol
FIG. 3. Colony counts for 416-145-50 at 1 mg/mL
FIG. 4. Colony counts for 416-145-50 at 500 ug/mL
FIG. 5 Colony counts for 1940601 in ionic o/w emulsion system at 0.5%
FIG. 6 Colony counts for 1940602 in ionic o/w emulsion system at 0.1%
Figure 2:
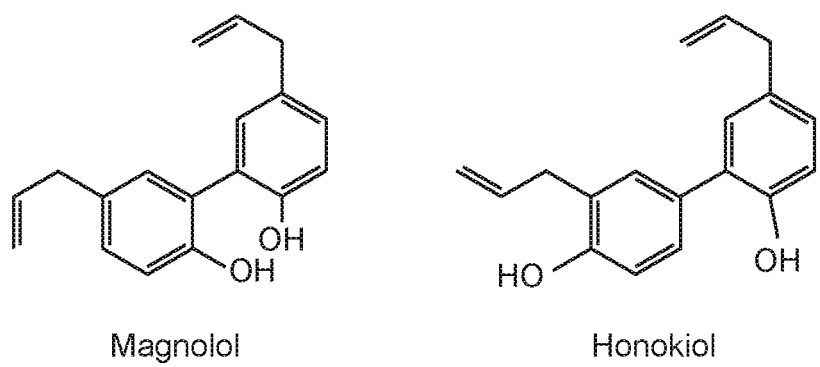

In brief, this disclosure and contemplated embodiments are directed to compounds and compositions which can be used as preservatives and anti-microbial agents, including stereoisomers, pharmaceutically or nutraceutically acceptable salts, tautomers, glycosides and prodrugs of the disclosed compounds, and to related methods. Contemplated embodiments relate to preservatives derived from extracts derived from *Albizia amara* seeds and *Magnolia officinalis* barks, which can be used to preserve food, cosmetics, nutraceuticals, oral hygiene products, and pharmaceuticals.

Contemplated compounds and compositions are derived from or comprise at least one plant extract, wherein the plant extract may or may not be enriched. As part of this development, frequently and acceptable assays were utilized to test contemplated compounds and compositions.

Specifically, compositions, compounds and methods for preservatives and antimicrobial compositions are disclosed that include a mixture of plant extracts, wherein the plant extracts comprise at least one *Albizia amara* seeds and at least one *Magnolia officinalis* barks.

A contemplated embodiment includes a preservative mixture or composition that comprises a mixture of at least one *Albizia* extract and at least one *Magnolia* extract. Yet another contemplated embodiment includes a composition that comprises a mixture of at least one *Albizia* extract enriched for one or more macrocyclic alkaloids and at least one *Magnolia* extract enriched for one or more lignans. In contemplated embodiments, compositions are considered preservatives, antimicrobial agents or combinations thereof.

Some contemplated embodiments comprise a mixture of at least one *Albizia* extract from a plant material or other source and at least one *Magnolia* extract from a plant material or another source, wherein the at least one *Albizia* extract has an increase in an amount or an activity of one or more macrocyclic alkaloids as compared to the amount or the activity of the one or more macrocyclic alkaloids in the plant material or another source of the at least one *Albizia* extract, and wherein the at least one *Magnolia* extract has an increase in an amount or an activity of one or more lignans as compared to the amount or the activity of the one or more lignans in the plant material or another source of the at least one *Magnolia* extract.

In some embodiments, the at least one *Albizia* extract and the at least one *Magnolia* extract are blended in a weight ratio ranging from about 10:1 to 1:10. In other embodiments, the at least one *Albizia* extract and the at least one *Magnolia* extract are blended in a weight ratio at about 1:1. Contemplated preservatives, compositions and mixtures can be utilized to preserve food, cosmetics, nutraceuticals and pharmaceuticals. These contemplated preservatives, compositions and mixtures can be provided in a range from about 0.001% to about 10% by weight of the total composition. In some embodiments, the range is from about 0.01% to about 5% by weight of the total composition. In other embodiments, the range is from about 0.1% to about 1% by weight of the total composition.

In addition, compositions, compounds and methods for preservatives and antimicrobial compositions are disclosed that include a mixture of plant extracts, wherein the plant extracts comprise at least one an *Albizia amara* seeds extract enriched for one or more macrocyclic alkaloids and a *Magnolia* bark extract enrich for one or more biphenolic lignans.

The concept of discovering a unique blend of compounds and extracts with enhanced antimicrobial activities was borrowed from the practice of combinations of antibiotics. The field of synergistic combinations of antibiotics is extremely broad and some fixed combinations were successfully developed commercially, with respect to their effects on treating infection with drug resistance. Through a high-throughput anti-*E. coli* screening of a plant library of over 10,216 organic extract and aqueous extracts, which are generated from medicinal plants collected from all over the world, *Albizia amara* seeds extract was identified as the best lead exhibiting potent anti-Gram negative inhibition with a MIC value of 40 ug/mL. Bioassay-guided isolation and identification confirmed the active components are budmunchimaine C and its analogues.

The *Albizia amara* seeds extract showed potent inhibition against both anti-Gram positive and anti-Gram-negative bacterial, but with mild anti-fungal activity against either *Candida albicans* or *Aspergillus brasiliensis*. To search for a composition effective against Gram-positive, Gram-negative and fungi required by category 2 preserve in USP chapter <51>, mainly targeting on boosting the anti-fungal activity, specifically against *C. albicans* and *A. brasiliensis*, the *Albizia amara* seeds extract was formulated with *Magnolia* barks extract for unexpected enhanced outcomes.

Surprisingly and unexpectedly, the additions of *Magnolia* bark extract caused a dramatic increase of its anti-fungal activity against both *C. albicans* and *A. brasiliensis*, and hence signify the importance of the combination of these two materials. The merit of combining these two plant materials were determined, and an unexpected synergy against both *C. albicans* and *A. brasiliensis* was observed with the beneficial effects exceeding the additive interaction based on the FCI index analysis. Collectively, it is contended that putting these two plants into the specific ratios provides a novelty to the composition as demonstrated in its remarkable antibacterial activity and effects.

An interesting synergy was discovered when *Albizia amara* seeds extract was blended with *Magnolia* bark extract at ratios of 1:3 and 1:1. These two plants were never combined together before at specific ratios to yield contemplated and disclosed bioactivities, which are generally understood as the unique combination in these contemplated embodiments.

The antibacterial activity and efficacy of Composition 1A:1M, where A stands for *Albizia amara* seeds extract and M for *Magnolia* barks extract, was evaluated following the USP <51> guideline. Composition 1A:1M, which is 1:1 ratio of *Albizia amara* seeds extract and *Magnolia* bark extract at a concentration of 1 mg/mL, significantly reduce the counts of *P. aeruginosa*, and *A. brasiliensis* with Log 10 reduction at 5.58 and 4.1 respectively and significantly, if not completely, eliminate *S. aureus*, *E. coli*, and *C. albicans* after 48 h, and no bacterial or fungi growth was observed after 7 days, 14 days, and 28 days against all five microorganisms. In fact, none of the constituents showed such potent and broad antimicrobial activity at the magnitude equivalent to the one shown for a contemplated compound or composition comprising *Albizia amara* and *Magnolia*. Furthermore, a contemplated and unique ratio of or about 1A:1M provides demonstrated effectiveness of this composition against all five microorganisms including *E. coli, P. aeruginosa, S. aureus, A. brasiliensis*, and *C. albicans*.

It is contemplated that the *Albizia* is derived, obtained or selected from at least one of the following—alone or in combination with one another: *Albizia amara, Albizia schimperiana, Albizia lebbek, Albizia gummifera, Albizzia inopinata, Albizia saman (Samanea saman=Pithecolobium saman), Albizia adianthifolia, Albizia adinocephala, Albizia anthelmintica, Albizia antunesiana, Albizia chevalieri, Albizia corniculata, Albizia crassiramea, Albizia duclouxii, Albizia glabra, Albizia julibrissin, Albizia kalkora, Albizia lebbekoides, Albizia myriophylla, Albizia nigricans, Albizia odoratissima, Albizia peterisana, Albizia poilanei, Albizia procera, Albizia tanganyicensis, Albizia vialeana pierre, Albizia zygia, Aphelandra fuscopunctata, Ephedra* spp., *Verbascum pseudonobile, Incarvillea sinensis, Verbascum phoenicum, Verbascum nigrum, Clerodendrum buchneri,* or *Aphelandra squarrosa*.

*Albizia amara* extract, as disclosed, is a contemplated component or constituent that can be utilized as part of a target compound or composition. *Albizia amara* extract may be obtained, derived or selected from any suitable source or sources, including *Albizia schimperiana, Albizia lebbek, Albizia gummifera, Albizzia inopinata, Albizia saman (Samanea saman=Pithecolobium saman), Albizia adianthifolia, Albizia adinocephala, Albizia anthelmintica, Albizia antunesiana, Albizia chevalieri, Albizia corniculata, Albizia crassiramea, Albizia duclouxii, Albizia glabra, Albizia julibrissin, Albizia kalkora, Albizia lebbekoides, Albizia myriophylla, Albizia nigricans, Albizia odoratissima, Albizia peterisana, Albizia poilanei, Albizia procera, Albizia tanganyicensis, Albizia vialeana pierre, Albizia zygia, Aphelandra fuscopunctata, Ephedra* spp., *Verbascum pseudonobile, Incarvillea sinensis, Verbascum phoenicum, Verbascum nigrum, Clerodendrum buchneri, Aphelandra squarrosa* or a combination thereof.

*Albizia amara* extract may be enriched for one or more macrocyclic alkaloids as contemplated herein. In some contemplated embodiments, the *Albizia* extract comprises about 0.01% to 99.9% of macrocyclic alkaloids. Contemplated alkaloids isolated from *Albizia* or *Albizia amara* extract are extracted with any suitable solvent, including water, methanol, ethanol, alcohol, a water-mixed solvent or a combination thereof, or with supercritical fluid. In contemplated embodiments, the *Albizia amara* extract comprises about 0.01% to about 99.9% macrocyclic alkaloids. Contemplated alkaloids isolated from *Albizia amara* extract are budmunchiamine A, B, C, D, E, F, G, H, I, J, K, budmunchiamine L1, L2, L3, L4, L5, L6, 13-normethylbudmunchiamine K, 9-normethylbudmunchiamine K, 1-normethylbudmunchiamine K, 6'-hydroxy-9-normethylbudmunchiamine K, 6'-hydroxybudmunchiamine K, Felipealbizine A, Felipealbizine B, 6'-hydroxybudmunchiamine C, Pithecolobine, Protomethine, Verbamethine, Verbametrine, Isoverbametrine, Isoverbamethine, Verbamekrine, Isoverbamekrine, Verbascine, Verbacine, Verbasitrine, Verballocine, Isoverbasitrine, Verballoscenine, Isoverbasikrine, N1-(Z)-p-Methoxycinnamoylbuchnerine, Buchnerine, Verbamedine, Verbascenine, Verbascenine, Isoverbamedine, Schweinine, Prelandrine, Incasine B', Incasine B or a combination thereof.

*Magnolia* extract is a contemplated component or constituent that can be utilized as part of a target compound or composition. *Magnolia* extract may be obtained from any suitable source, including *Magnolia officinalis, Magnolia acuminate, Magnolia biondii, Magnolia coco, Magnolia denudate, Magnolia fargesii, Magnolia garrettii, Magnolia grandiflora, Magnolia henryi, Magnolia liliflora, Magnolia kachirachirai, Magnolia kobus, Magnolia obovata, Magnolia praecocissima, Magnolia pterocarpa, Magnolia pyramidata, Magnolia rostrate, Magnolia salicifolia, Magnolia sieboldii, Magnolia soulangeana, Magnolia stellate, Magnolia virginiana*, prod. of degradation of birch lignin, *Acanthus ebracteatus, Aptosimum spinescens, Aralia bipinnata, Araucaria angustifolia, Araucaria araucana, Artemisia absinthium, Haplophyllum acutifolium, Haplophyllum perforatum, Liriodendron tulipifera, Krameria cystisoides, Perilla frutescens, Lawsonia inermis Myristica fragrans* (nutmeg), *Parakmeria yunnanensis* (preferred genus name *Magnolia*), *Persea japonica, Piper futokadsura, Piper wightii, Rollinia mucosa, Sassafras randaiense, Scrophularia albida-colchica, Stellera chamaejasme, Syringa velutina, Syzygium cumini, Talauma gloriensis, Virola elongate, Urbanodendron verrucosum, Wikstroemia sikokiana* or a combination thereof.

*Magnolia* extract may be enriched for one or more lignans, including diphenol lignans, as contemplated herein. Contemplated lignans isolated from *Magnolia* extract are extracted with any suitable solvent, including water, methanol, ethanol, alcohol, a water-mixed solvent or a combination thereof or with supercritical fluid.

In contemplated embodiments, the *Magnolia* extract comprises about 0.01% to about 99.9% diphenol lignans, biphenolic lignans or a combination thereof. Contemplated lignans isolated from *Magnolia* extract are magnolol, honokiol, Biondinin A, 2,3-Bis(4-hydroxy-3-methoxyphenyl)-2-propenal, Denudadione C, Clovanemagnolol, 8-[2-Hydroxy-5-(2-propenyl)phenyl]-6-(2-propenyl)-2H-1-benzopyran-2-one, Denudanolide C, Denudanolide D, Denudanolide B, Denudanolide A, Denudatin A, Denudatin B; (+)-form, 4-Hydroxy-6'-methoxy-3,3'-biligna-7,7'-diene-9,9'-dial, 4'-Methoxymagndialdehyde, 5,5'-Di-2-propenyl-[1,1'-biphenyl]-2,2'-diol, 2,2'-Bichavicol, FEMA 4559, 5,5'-Diallyl-2,2'-dihydroxybiphenyl, Bornylmagnolol, 5,5'-Diallyl-2-(3-methyl-2-butenyloxy)biphenyl-2'-ol, 5,5'-Diallyl-2-(allyloxy)biphenyl-2'-ol, 3',5-Diallyl-2,4'-dihydroxybiphenyl, 3',5-Di-2-propenyl-2,4'-biphenyldiol, 5-Allyl-3'-(1-propenyl)biphenyl-2,4'-diol, 3'-(1-Propenyl)-5-(2-propenyl)-2,4'-biphenyldiol, 3',5-Diallyl-2-hydroxy-4'-methoxybiphenyl, 4'-O-Methylhonokiol, 2-Hydroxy-4'-methoxy-3',5-di-2-propenylbiphenyl, 4,4'-Diallyl-2,3'-dihydroxydiphenyl ether, 2-[3-Hydroxy-4-(2-propenyl)phenoxy]-5-(2-propenyl)phenol, 2-Hydroxy-3-methoxy-4',5-di-2-propenyldiphenyl ether, 4',5-Diallyl-2-hydroxy-3-methoxydiphenyl ether, 2-Methoxy-4-(2-propenyl)-6-[4-(2-propenyl)phenoxy]phenol, Fargesin, Methyl pluviatilol, 3,4-Dimethoxy-3',4'-methylenedioxy-7,9':7',9-diepoxylignan, Kobusin, Desmethoxyaschantin, O-Methylpiperitol, Spinescin, (+)-Fargesin, Planinin, Methylpluviatilol, Parakmerin A, 6-Allyl-7-(3,4-dimethoxyphenyl)-2,3-dimethoxy-8-methyl-tricyclo[4.2.0.0.$^{2,8}$]oct-3-en-5-one, Magnosalin, Dipiperitylmagnolol, Kachirachirol B, Acuminatin, Licarin D, Eudeshonokiol A, Eudesmagnolol, Eudesmin; (+)-formm, (+)-Epieudesmin, (−)-Epieudesmin, Kachirachirol A, Eupomatenoid 13, Fargesiphenol B, Fargesiphenol C, Fargesone A, Fargesone B, 4,5-Dimethoxy-3',4'-methylenedioxy-2,7'-dioxo-5,8'-ligna-3,6,8-triene, 4-(1,3-Benzodioxol-5-yl)-2,3,4,5-tetrahydro-7-methoxy-5-methyl-8H-2,5a-methano-1-benzoxepin-8-one, Garrettilignan A, Garrettilignan B, Tetrahydro-4-(3-hydroxy-4,5-dimethoxyphenyl)-1H, 3H-furo[3,4-c]furan-1-one, Kachiranol, 7',9-Dihydroxy-3,3',4,4',5-pentamethoxy-7,9'-epoxylignan, Magnone B, 3,3', 4,4',5,9-Hexamethoxy-7,9'-epoxylignan-7'-one, Magnolenin C, 3',4,7,9,9'-Pentahydroxy-3,5'-dimethoxy-8,4'-oxyneolignan, 3,3'-Dimethoxy-4,5:4',5'-bis(methylenedioxy)pyramidatin, 3'-Hydroxy-3,4,4',5,5'-pentamethoxypyramidatin, Pyramidatin B, 3,3',4',5'-Tetramethoxy-4,5-methylenedioxypyramidatin, 3,3',4,4',5,5'-Hexamethoxypyramidatin, Pyramidatin C, Pyramidatin, Pyramidatin D, 3-Hydroxy-3',4,4',5,5'-pentamethoxypyramidatin, Pyramidatin A, 3-Hydroxy-3',4,5-trimethoxy-4',5'-methylenedioxypyramidatin, Pyramidatin F, Pyramidatin G, Pyramidatin H, Pyramidatin E, 5'-Hydroxy-3,3',4,4',5-pentamethoxypyramidatin, Magnoshinin, 2',3,4,4',5,6-Hexamethoxy-2,7'-cyclolign-7-ene, Acanthoside B, Eleutheroside E1, 3-Hydroxy-3',4,4',5,5'-pentamethoxy-7,9':7',9-diepoxylignan, (+)-Episyringaresinol, Lirioresinol A, Symplicosigenol, Kobusinol B, Fargesol, 9-O-Acetylfargesol, Magnolone, Biondinin B, Biondinin E, Magnone A, 7,9,9'-Trihydroxy-3,3',4-trimethoxy-8,4'-oxyneolignan, erythro-form, threo-form, Magnovatin A, Magnovatin B, Oleiferin C, 3,4:3',4'-Bis(methylendioxy)-7-lignanol, 7-Hydroxy-3,4:3',4'-bis(methylenedioxy)lignan, Liliflodione, Denudadione B, Denudadione A, Liliflol A, Liliflol B, Denudatone, 3-[2',6-Dihydroxy-5'-(2-propenyl)[1,1'-biphenyl-3-yl]]-2-propenal, Randainal, Magnaldehyde B, Magnaldehyde C, 6'-O-Methylmagnaldehyde B, 4-Deoxy-6-methoxymagnaldehyde A, 4-Methoxymagnaldehyde B, 2',6-Dihydroxy-5'-(2-propenyl) [1,1'-biphenyl]-3-carboxaldehyde, 5-Allyl-5'-formyl-2,2'-dihydroxybiphenyl, Magnaldehyde E, 6-O-Methylmagnaldehyde E, 9-Hydroxy-3,3',4,4',5-pentamethoxy-7,9'-epoxylign-7'-ene, 9,9'-Dihydroxy-3,3',4, 4',5-pentamethoxy-2,7'-cyclolign-7-ene, Magnolianin, Magnolignan I, Magnolignan B, Magnolignan A, Magnolignan D, Magnolignan C 6'-glucoside, Magnolignan C, Magnolignan E, Magnolignan F, Magnolignan G, Magnolignan H, 2-[4-Hydroxy-3-(2-propenyl)phenyl]-2,5-cyclohexadiene-1,4-dione, 2-(3-Allyl-4-hydroxyphenyl)-1,4-benzoquinone, Magnosalicin; (7RS,7'SR,8RS,8'RS)-form, Magnostellin B, Magnostellin B; 7,9-Diepimer, 5-methoxy, 5[2-Hydroxy-5-(2-propenyl)phenyl]-2-methylbenzofuran, 3-Hydroxy-3',4,4',5-tetramethoxy-7,9',7',9-diepoxylignan, 3-De-O-methylmagnolin, Magnolin, 3-O-Demethylaschantin, 3'-O-Demethylaschantin, 3-Hydroxy-4,5-dimethoxy-3', 4'-methylenedioxy-7,9':7',9-diepoxylignan, 5'-Hydroxy-4'-O-methylpiperitol, Epimagnolin A, 7'-Hydroxy-3,3',4,4'-tetramethoxy-7,9'-epoxylignan, Magnostellin A, Kobusinol A, 4,7'-Dihydroxy-3,3',4'-trimethoxy-7,9'-epoxylignan, 4',5, 9-Trihydroxy-3,3'-dimethoxy-7,9'-epoxylignan, Fargesiphenol A, Liliflone, Monoterpenylmagnolol, Piperitylhonokiol, Monoterpenylhonokiol, Saulangianin I, Sesamin; (−)-form, Syringinoside, Syringin 4"-glucoside, 3,3',4,5'-Tetramethoxy-7,9':7',9-diepoxylignan, 3',5'-Dimethoxy-3,4-methylenedioxy-7,9':7',9-diepoxylignan, Galgravin, 2,2'-Dihydroxy-3-methoxy-5,5'-di-2-propenylbiphenyl, 3-Methoxymagnolol, 5,5'-Diallyl-2,2'-dihydroxy-3-methoxybiphenyl or a combination of any of these thereof.

Contemplated compounds, medicinal compositions and compositions may comprise or additionally comprise or consist of at least one antimicrobial ingredient. In some embodiments, the at least one antimicrobial ingredient may comprise or consist of plant powder or plant extract of *Psoralea corylifolia*, Curcumin, *Curcuma longa*, Eugenol,

*Alpinia galganga, coptidis, Azadirachta indica*, Propolis, clove oil, *Sophora flavescens, Areca catechu, Glycyrrhiza glabra, Thuja plicata*, Cortex *phellodendri*, *Rheum* palate, *Alpinia officinarum, Broussonetia papyriferra, Viburnum cotinifolium, Euphorbia hirta linn, Vitex negundo*, or a combination thereof.

Contemplated compounds, medicinal compositions and compositions may comprise or additionally comprise, consist of or consist essentially of at least one or more known antimicrobial preservatives, constituents or ingredients. In some embodiments, the at least one antimicrobial ingredient may comprise or consist of calcium propionate, sodium benzoate, sodium nitrate, sodium nitrite, potassium sorbate, benzoic acid, salicylic acid, sorbic acid, alcohol, penoxyethanol, 1,2-diol alcohol (1,2 propanediol, 1,2 butanediol, 1,2 pentanediol, 1,2-hexanediol), 1,3-diol alcohol (1,3 propanediol, 1,3 butanediol, 1,3 pentaneidol, 1,3-hexanediol), 1,5 pentanediol, benzakonium chloride, parabens, sulfites (sulfur dioxide, sodium bisulfite, potassium hydrogen sulfite, etc.) and disodium EDTA, and BHT (butylated hydroxy toluene) and BHA (butylated hydroxyl).anisole), formaldehyde (usually in solution), glutaraldehyde (kills insects), and methylchloroisothiazolinone.

The composition further comprises a pharmaceutically or nutraceutically or cosmetically acceptable carrier, diluent, or excipient, wherein the pharmaceutical or nutraceutical formulation comprises from about 0.001 weight percent (wt %) to about 10 wt % of the active ingredients of the extract mixture. These contemplated active ingredients can be provided in a range from about 0.001% to about 10% by weight of the total composition. In some embodiments, the range is from about 0.01% to about 5% by weight of the total composition. In other embodiments, the range is from about 0.1% to about 1% by weight of the total composition.

Also, contemplated herein are preservatives or antimicrobial agents of the disclosed compounds. Such products may result from, for example, the oxidation, reduction, hydrolysis, amidation, esterification, and the like of the administered compound, primarily due to enzymatic processes. Accordingly, contemplated compounds are those produced by a process comprising administering a contemplated compound or composition to a mammal for a period of time sufficient to yield a metabolic product thereof. Such products are typically identified by administering a radiolabeled compound of this disclosure in a detectable dose to an animal, such as rat, mouse, guinea pig, dog, cat, pig, sheep, horse, monkey, or human, allowing sufficient time for metabolism to occur, and then isolating its conversion products from the urine, blood or other biological samples.

As used herein, the phrases "stable compound" and "stable structure" are used interchangeably and used to indicate a compound that is sufficiently robust to survive isolation to a useful degree of purity from a reaction mixture, and to survive formulation into an efficacious therapeutic agent.

As used herein, the term "mammal" includes humans and both domestic animals, such as laboratory animals or household pets (e.g., rat, mouse, guinea pig, cats, dogs, swine, cattle, sheep, goats, horses, rabbits, primates), and non-domestic animals, such as wildlife or the like.

As used herein, the terms "optional" or "optionally" may be used interchangeably and mean that the subsequently described element, component, event or circumstances may or may not occur, and includes instances where the element, component, event or circumstance occur and instances in which they do not. For example, "optionally substituted aryl" means that the aryl radical may or may not be substituted—in other words, the description includes both substituted aryl radicals and aryl radicals having no substitution.

Contemplated compounds, medicinal compositions and compositions may comprise or additionally comprise or consist of at least one pharmaceutically or nutraceutically or cosmetically acceptable carrier, diluent or excipient. As used herein, the phrase "pharmaceutically or nutraceutically or cosmetically acceptable carrier, diluent or excipient" includes any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Contemplated compounds, medicinal compositions and compositions may comprise or additionally comprise or consist of at least one pharmaceutically or nutraceutically or cosmetically acceptable salt. As used herein, the phrase "pharmaceutically or nutraceutically or cosmetically acceptable salt" includes both acid addition and base addition salts.

As used herein, the phrase "pharmaceutically or nutraceutically or cosmetically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, or the like.

As used herein, the phrase "pharmaceutically or nutraceutically or cosmetically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include the sodium, potassium, lithium, ammonium, calcium, magnesium, iron, zinc, copper, manganese, aluminum salts and the like. In certain embodiments, the inorganic salts are ammonium, sodium, potassium, calcium, or magnesium salts. Salts derived from organic bases include salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-dieethylaminoethanol, dicyclohexylamine, lysine, arginine, histidine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly useful organic bases include isopropylamine, diethylamine, ethanolamine, trimethylamine, dicyclohexylamine, choline, or caffeine.

Often crystallizations produce a solvate of or include contemplated compounds. As used herein, the term "solvate" refers to an aggregate that comprises one or more molecules of a contemplated compound, medicinal composition or composition with one or more molecules of solvent. The solvent may be water, in which case the solvate may be a hydrate. Alternatively, the solvent may be an organic solvent. Thus, the contemplated compounds, medicinal compositions or compositions may exist as a hydrate, including a monohydrate, dihydrate, hemihydrate, sesquihydrate, trihydrate, tetrahydrate and the like, as well as the corresponding solvated forms. A contemplated compound, medicinal composition or composition may be a true solvate, while in other cases, a contemplated compound, medicinal composition or composition may merely retain adventitious water or be a mixture of water plus some adventitious solvent.

A preservative or antimicrobial agent refers to a formulation of a contemplated compound, composition or medicinal composition and a medium generally accepted in the art for the delivery of the antimicrobial activity in food, cosmetics, nutraceuticals, oral hygiene products, and pharmaceuticals. For example, a contemplated preservative compound, or composition may be formulated or used as a stand-alone composition, or as a component in a prescription drug, an over-the-counter (OTC) medicine, a botanical drug, an herbal medicine, a homeopathic agent, or any other form of health care product reviewed and approved by a government agency. Exemplary and contemplated preservative compositions may be formulated or used as a stand-alone composition, or as a nutritional or bioactive component in food, a novel food, a functional food, a beverage, a bar, a food flavor, a food additive, a medical food, a dietary supplement, or an herbal product. A medium generally accepted in the art includes all pharmaceutically or nutraceutically acceptable carriers, diluents or excipients therefor.

In some embodiments, contemplated compositions are formulated as a tablet, hard capsule, soft gel capsule, powder, granule, liquid, tincture, sashay, ready to drink shot, or lozenge, cosmetic cream, gel, lotion, shampoo, hire conditioner, body rinse, body lotion, hire color agent, skin color agent, eye color agent, lip bum, perfume, toothpaste, mouth washing, fruit juice, aloe juice, yogurt, foods, soft drink, beverage, processed fruits, chees products, wine, gem, peanut butter, RTD, protein bar, or a snack bar.

As used herein, the phrase "enriched for" refers to a plant extract or other preparation having at least about a two-fold up to about a 1000-fold increase in the amount or activity of one or more active compounds as compared to the amount or activity of the one or more active compounds found in the weight of the plant material or other source before extraction or other preparation. In certain embodiments, the weight of the plant material or other source before extraction or other preparation may be dry weight, wet weight, or a combination thereof.

As used herein, "major active ingredient" or "major active component" refers to one or more active contemplated compounds found in a plant extract or other preparation, or enriched for in a plant extract or other preparation, which is capable of at least one biological activity. In certain embodiments, a major active ingredient of an enriched extract will be the one or more active compounds that were enriched in that extract. Generally, one or more major active components will impart, directly or indirectly, most (i.e., greater than 50%) of one or more measurable biological activities or effects as compared to other extract components. In certain embodiments, a major active ingredient may be a minor component by weight percentage of an extract (e.g., less than about 50%, 25%, 20%, 15%, 10%, 5%, or 1% of the components contained in an extract) but still provide most of the desired biological activity. Any contemplated composition containing a major active ingredient may also contain minor active ingredients that may or may not contribute to the pharmaceutical or nutraceutical activity of the enriched composition, but not to the level of major active components, and minor active components alone may not be effective in the absence of a major active ingredient.

As used herein, the phrases "effective amount" or "therapeutically effective amount" refer to that amount of a contemplated compound, medicinal composition or composition that, when used in food, cosmetics, nutraceuticals, oral hygiene products, and pharmaceuticals, is sufficient to prevent the degradation of bacterial and inhibit the growth of bacteria, fungi and other microorganisms.

The chemical naming protocol and any structure diagrams used herein are a modified form of the I.U.P.A.C. nomenclature system, using the ACD/Name Version 9.07 software program or ChemDraw Ultra Version 11.0 software naming program (CambridgeSoft), wherein the compounds of this disclosure are named herein as derivatives of the central core structure, e.g., the imidazopyridine structure. For complex chemical names utilized herein, a substituent group is named before the group to which it attaches. For example, cyclopropylethyl comprises an ethyl backbone with cyclopropyl substituent.

A contemplated preservative composition may be in the form of a solid or liquid. In one aspect, the carrier(s) are particulate, so that the compositions are, for example, in tablet or powder form. The carrier(s) may be liquid, with the compositions being, for example, oral syrup, injectable liquid or an aerosol, which is useful in, for example, inhalatory administration.

When intended for oral administration, the pharmaceutical or nutraceutical composition is in either solid or liquid form, where semi solid, semi liquid, suspension and gel forms are included within the forms considered herein as either solid or liquid.

As a solid composition for oral administration, the preservative composition may be formulated into a powder, granule, compressed tablet, pill, capsule, chewing gum, wafer, bar, or like form. Such a solid composition will typically contain one or more inert diluents or edible carriers. In addition, one or more of the following may be present: binders such as carboxymethylcellulose, ethyl cellulose, cyclodextrin, microcrystalline cellulose, gum tragacanth or gelatin; excipients such as starch, lactose or dextrins, disintegrating agents such as alginic acid, sodium alginate, Primojel®, corn starch and the like; lubricants such as magnesium stearate or Sterotex®; glidants such as colloidal silicon dioxide; sweetening agents such as sucrose or saccharin; a flavoring agent such as peppermint, methyl salicylate or orange flavoring; and a coloring agent.

A contemplated preservative composition may be in the form of a capsule, for example, a gelatin capsule, it may contain, in addition to materials of the above type, a liquid carrier such as polyethylene glycol or oil.

A contemplated preservative composition may be in the form of a liquid, for example, an elixir, syrup, gel, solution, emulsion or suspension. The liquid may be for oral administration or for delivery by injection, as two examples. When intended for oral administration, a useful composition contains, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A contemplated liquid preservative compositions, whether they be solutions, suspensions or other like form, may include one or more of the following adjuvants: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a generally useful adjuvant. An injectable pharmaceutical or nutraceutical composition is sterile.

A contemplated liquid preservative composition intended for either parenteral or oral administration should contain an amount of a contemplated compound, medicinal composition or composition such that a suitable dosage will be obtained.

A contemplated preservative composition may be intended for topical administration, in which case the carrier may suitably comprise a solution, emulsion, cream, lotion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical or nutraceutical composition for topical administration. If intended for transdermal administration, the composition may include a transdermal patch or iontophoresis device.

A contemplated preservative composition may be intended for rectal administration, in the form, for example, of a suppository, which will melt in the rectum and release the drug. The composition for rectal administration may contain an oleaginous base as a suitable nonirritating excipient. Such bases include lanolin, cocoa butter and polyethylene glycol.

A contemplated preservative composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

A contemplated preservative composition in solid or liquid form may include an agent that binds to the contemplated compound and thereby assists in the delivery of the compound. Suitable agents that may act in this capacity include a monoclonal or polyclonal antibody, a protein or a liposome.

A contemplated preservative composition in solid or liquid form may include reducing the size of a particle to, for example, improve bioavailability. The size of a powder, granule, particle, microsphere, or the like in a composition, with or without an excipient, can be macro (e.g., visible to the eye or at least 100 µm in size), micro (e.g., may range from about 100 µm to about 100 nm in size), nano (e.g., may no more than 100 nm in size), and any size in between or any combination thereof to improve size and bulk density.

A contemplated preservative composition may be prepared by methodology well known in the preservative art. For example, a preservative composition intended to be administered by injection can be prepared by combining a contemplated compound with sterile, distilled water so as to form a solution. A surfactant may be added to facilitate the formation of a homogeneous solution or suspension. Surfactants are compounds that non-covalently interact with a contemplated compound so as to facilitate dissolution or homogeneous suspension of the compound in the aqueous delivery system.

Contemplated compounds, compositions and medicinal compositions, or their pharmaceutically or nutraceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Contemplated compounds, compositions and medicinal compositions, or pharmaceutically or nutraceutically acceptable derivatives thereof, may also be administered simultaneously with, prior to, or after administration of one or more other therapeutic agents. Such combination therapy includes administration of a single pharmaceutical or nutraceutical dosage formulation that contains a contemplated compound and one or more additional active agents, as well as administration of a contemplated compound and each active agent in its own separate pharmaceutical or nutraceutical dosage formulation. For example, a contemplated compound and another active agent can be administered to the patient together in a single oral dosage composition, such as a tablet or capsule, or each agent can be administered in separate oral dosage formulations. Where separate dosage formulations are used, contemplated compounds and one or more additional active agents can be administered at essentially the same time, i.e., concurrently, or at separate staggered times, i.e., sequentially; combination therapy is understood to include all these regimens.

It is understood that in the present description, combinations of substituents or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include C(O)R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, Protective Groups in Organic Synthesis (1999), 3rd Ed., Wiley, which is incorporated by reference herein in its entirety. As one of skill in the art would appreciate, a protecting group may also be a polymer resin such as a Wang resin, Rink resin or a 2-chlorotrityl-chloride resin.

It will also be appreciated by those skilled in the art, although such protected derivatives of contemplated compounds may not possess pharmacological activity as such, they may be administered to a mammal and thereafter metabolized in the body to form compounds which are pharmacologically active. Such derivatives may therefore be described as "prodrugs". All prodrugs of contemplated compounds are included within the scope of this disclosure.

Furthermore, contemplated compounds that exist in free base or acid form can be converted to their pharmaceutically or nutraceutically acceptable salts by treatment with the appropriate inorganic or organic base or acid by methods known to one skilled in the art. Salts of contemplated compounds can be converted to their free base or acid form by standard techniques.

In some embodiments, contemplated compounds, compositions and/or medicinal compositions can be isolated from plant sources, for example, from those plants included in the examples and elsewhere throughout the present application. Suitable plant parts for isolation of contemplated extracts and compounds include leaves, bark, trunk, trunk bark, stems, stem bark, twigs, tubers, root, root bark, bark surface (such as periderm or polyderm, which may include phellem, phellogen, phelloderm, or any combination thereof), young shoots, rhizomes, seed, fruit, androecium, gynoecium, calyx, stamen, petal, sepal, carpel (pistil), flower, or any combination thereof. Contemplated plant extracts are derived from at least one plant part selected from the group consisting of stems, stem barks, trunks, trunk barks, twigs, tubers, roots, root barks, young shoots, seeds, rhizomes, flowers and other reproductive organs, tissue cultures and stem cell cultures, leaves, other aerial parts or a combination thereof. In some related embodiments, contemplated compounds are isolated from plant sources and synthetically modified to contain any of the recited substituents. In this regard, synthetic modification of contemplated compounds isolated from plants can be accomplished using any number of techniques that are known in the art and are well within the knowledge of one of ordinary skill in the art.

EXAMPLES

Example 1

Preparation of Organic Extracts

Dried ground plant materials (20 g) were loaded into two 100 mL stainless steel tubes and extracted twice with an organic solvent mixture (methylene chloride/methanol in a ratio of 1:1) using an ASE 300 automatic extractor at 80° C. and pressure 1500 psi. The extract solution is automatically filtered and collected. The organic extract solution is evaporated with rotary evaporator to give crude organic extract (OE). The stainless steel tube were flushed with fresh solvent and purged with nitrogen gas to dryness before switching to aqueous extraction at 50° C. The aqueous solution was filtered and freeze-dried to provide aqueous extract (AE).

Example 2

High Throughput Screening for Anti-Microbial Activity Against Escherichia coli

The plant library with 10, 216 OE and AE were screened for antimicrobial activity against E coli with a high throughput screening in 96-well microtiter plates. Microbial cultures E. coli KCTC2571 (=ATCC8739) was used as the test microorganisms. LB broth was used as the diluent or media in the wells. Cultures of bacteria were incubated for 24 h at 37° C. The plant library samples were screened in duplicate for each sample at a concentration of 250 ug/mL. 180 ul of E coli culture was added in each well with inoculum size of $3\times10^5$ CFU/mL and mixed with 20 ul test sample. 200 ul bacterial cultures without treatment were used as control with 200 ul LB broth as blank. Cultures of bacteria were incubated for 24 h at 37° C. and OD was measured at 600 nm for each sample. The inhibition was calculated based on the following equation. Grape seeds extract was used as positive control. The preliminary results showed 82 extracts with over 80% inhibitions at 250 ug/mL, which were further tested at 50 ug/mL. 11 plant extracts exhibited 80% or higher inhibition at the concentration of 50 ug/mL. $MIC_{99}$ values were determined for those 11 hits, using the same method with serial dilutions. The plant hits were selected for further development based on the MIC values. Albizia amara seed was the top hit selected from this screening with potent anti-E. coli activity with a $MIC_{99}$ value at 12.5 ug/mL.

$$\text{Inhibition}(\%) = \frac{\text{Control} - (\text{Sample} - \text{Blank})}{\text{Control}} \times 100$$

Example 3

Preparation of Organic Extracts from Albizia amara Seeds

A total of 100 grams of dried Albizia amara seed powder are loaded into five 100 mL stainless steel tube and extracted twice with methanol using an ASE 350 automatic extractor at 80 degree and pressure 1500 psi. The extract solution is automatically filtered and collected. The organic extract solution is evaporated with rotary evaporator to give crude organic extract (OE) (25.1 g, 25.1%).

Similar results were obtained using the same procedure, but with the organic solvent being replaced with methanol or ethanol to provide a methanol extract (ME) or ethanol extract (EE), methanol:$H_2O$ (7:3) extracts, methanol:$H_2O$ (1:1) extracts, methanol:$H_2O$ (3:7) ethanol:$H_2O$ (7:3) extracts, ethanol:$H_2O$ (1:1) extracts, ethanol:$H_2O$ (3:7) extracts and water extracts respectively.

TABLE 1

The Albizia amara seed extracts extracted with different solvents

| Collect ID | Species | Parts | Ext_ID | Extraction Yield (%) | Solvent |
|---|---|---|---|---|---|
| R00557 | Albizia amara | Seed | RN368-28-01 | 27.6 | Water |
| | | | RN368-29-01 | 24.5 | MeOH |
| | | | RN368-29-02 | 26.5 | 50% MeOH/H2O |

Example 4

Fractionation, Purification and Identification and Quantification of Active Compounds from Albizia amara Seeds Extracts Bioassay guided isolation lead to the isolation and identification of the active macrocyclic alkaloid budmunchiamine C. 2 g Albizia seeds methanol extract was loaded to a C18 packed open column eluted with a solvent system of mixture of MeOH and 0.05% trifluoroacetic acid in water in a range of 55% MeOH to 75% MeOH. 9 fractions were collected. The active fraction 40 mg was dissolved in water 4 mL. Then Ethyl acetate 8 mL was added to the sample. After centrifuge, the lower layer was collected and this procedure will be repeated for three times. Then the sample will be dissolved in ammonium hydroxide water 4 mL with a PH value of 11 and washed with ethyl acetate 8 mL for three times to give the budmunchiamine C (23.5 mg). Methanol/ethanol was selected as the final solvent for extraction because methanol or ethanol extract showed highest alkaloid contents in the final extraction.

Budmunchiamine C content in the extracts extract by different solvent system could be analyzed by HPLC method with using a RP-C18 column (Phenomenex, 4.6×250 mm, 5 μm), with a gradient elution by methanol and 0.5% TFA in Water at a flow rate of 1 mL/min detected by UV detector at 210 nm or ELSD detector. Budmunchiamine C peak was identified based on the comparison with standard compound isolated and identified in house. Methanol extract (RN368-29-01) has the highest budmunchiamine C content compared with water, and 50% Methanol/$H_2O$ extracts, and showed the best anti-$E.$ $coli$ activity with a MIC value of 40 ug/mL. This result is consistent with the discovery and identification budmunchiamine C and its analogues as the active components responsible for the anti-Gram Negative bacterial activity of this plant. The budmunchiamines content in the plant extracts from different species, parts and collected from different location and season could be varied in a range of 0-6%. The methanol extract of the *Albizia amara* seeds was identified as the good source for budmunchiamine type alkaloids.

TABLE 2

Budmunchiamine C content and MIC against *E. coli* of the *Albizia amara* seed extracts

| Extract ID | Extraction | Budmunchiamine C | MIC (ug/mL) |
|---|---|---|---|
| RN368-29-01 | Methanol extract | 1.8% | 40 |
| RN368-29-02 | 50% Methanol/water extract | 1.6% | 100 |
| RN368-28-01 | Water extract | 1.1% | 100 |

Example 5

Anti-Microbial Activities of Different *Albizia* Species

To search for the *Albizia* material with good anti-Gram negative bacterial activity, *Albizia* plants of different species and different parts were collected from several countries including China, India, Pananma, Gana and Zimbabwe with diverse geological locations. The anti-*E. coli* activity was evaluated and MIC values were determined for the extracts of each *Albizia* material following the protocol as depicted in Example 2 with the anti-microbial activities results shown in Table 3.

TABLE 3 in vitro Anti-*E. coli* activity of *Albizia* extracts

| Plant species | Collect ID | Plant parts | Country origin | MIC (ug/mL) |
|---|---|---|---|---|
| A. amara | R00557 | seeds | India | 40 |
| A. amara | R00224 | seeds | Zimbabwe | >100 |
| A. julibrissin | R00558 | seeds | China | >100 |
| A. lebbeck | R00584 | seeds | India | >100 |
| A. procera | R00585 | seeds | India | >100 |
| A. richardiana | R00600 | seeds | India | >100 |

TABLE 3-continued in vitro Anti-*E. coli* activity of *Albizia* extracts

| Plant species | Collect ID | Plant parts | Country origin | MIC (ug/mL) |
|---|---|---|---|---|
| A. falcataria | R00610 | seeds | India | >100 |
| A. amara | R00581 | Leaf | India | >100 |
| A. amara | R00582 | Bark | India | >100 |
| A. amara | R00583 | Root | India | >100 |
| A. petersana | R00226 | Root bark | Zimbabwe | >100 |
| A. gumifera | R00225 | Stem bark | Zimbabwe | >100 |
| A. julibrissin | R00554 | Flower | China | >100 |
| A. julibrissin | R00555 | Bark | China | >100 |
| A. kalkora | R00567 | Bark | China | >100 |
| A. lebbeck | R00568 | Bark | China | >100 |
| A. lebbeck | E1373 | Bark | India | >100 |
| A. amara | R00581 | Leaf | India | >100 |
| A. amara | R00582 | Bark | India | >100 |
| A. amara | R00583 | Root | India | >100 |
| A. seman | P03417 | Leaf | Panama | 250 |
| A. seman | P01124 | Leaf | Ghana | >150 |
| A. seman | P01125 | Root bark | Ghana | 150 |
| A. seman | P01126 | Stem bark | Ghana | 150 |

Example 6

Antimicrobial Activity of *Albizia amara* Seeds Extract and Budmunchiamine C

Minimum Inhibitory Concentration against bacterial *S. aureus, P. aeruginosa, E. coli*, and fungi *A. brasiliensis* and *C. albicans* were determined for *Albizia amara* seeds extract and the active marker compound budmunchiamine C. The Minimum Inhibitory Concentration Method (MIC) is carried out following the general microbiological protocol to measure the lowest level of an antimicrobial agent that can inhibit microbial proliferation in liquid. Test microorganisms are prepared in liquid culture medium for bacteria or on agar for fungi. Suspensions of test microorganisms are standardized by dilution in appropriate broth solution, usually Mueller-Hinton broth. The test substance is prepared by conducting several serial 1:1 dilutions in a 96-well microtiter plate or in small test tubes, through Mueller-Hinton broth or other appropriate medium. All wells or tubes containing diluted test substances are inoculated with test microorganisms, individually, resulting in one additional and final dilution of the product in all test vessels. The microtiter plate or test tubes are incubated for 18-24 hours. After the incubation period, observations are made to determine the minimum concentration (MIC) which is the lowest concentration of test substance in a well where no turbidity (indicative of test microorganism growth) is observed and minimum bactericidal concentration (MBC).

The *Albizia amara* seeds extract RN368-31-MIX and budmunchiamine C were tested against five microorganisms required for category 2 including *Staphylococcus aureus* (ATCC 6538), *Escherichia coli* (ATCC 8739), *Pseudomonas aeruginosa* (ATCC 9027), *Candida albicans* (ATCC 10231), *Aspergillus brasiliensis* (ATCC 16404). Both *Albizia amara* seeds extract and budmunchiamine C showed potent anti-*E coli* activity with MIC values at 62.5 ug/mL for the seed extract, and 31.25 for budmunchiamine C. Relatively weaker anti-fungal activities were observed for the seed extract and budmunchiamine C. Budmunchiamine C was further tested against six other microorganisms with both MIC and MBC results shown in Table 5. Budmunchiamine C showed the most potent efficacy against *Streptococcus pyogenes* with a MIC of <0.97 ug/mL. It also showed significant efficacies against *Trichophyton mentagrophytes, Trichophyton rubrum, Propionibacterium acnes,* and *Staphylococcus epidermis.*

TABLE 4

Anti-microbial activities of *Albizia amara* seeds extract RN368-31-MIX and budmunchiamine C.

|  |  | Budmunchiamine C | |
|---|---|---|---|
| Organism | RN368-31-MIX MIC (ug/mL) | MIC (ug/mL) | MBC (ug/mL) |
| *Staphylococcus aureus* | 125 | 31.25 | 31.25 |
| *Escherichia coli* | 62.5 | 31.25 | 31.25 |
| *Pseudomonas aeruginosa* | 250 | 62.5 | 62.5 |
| *Candida albicans* | negative | * | 125 |
| *Aspergillus brasiliensis* | 500 | 125 | * |

* Unable to be determined

TABLE 5

Anti-microbial activities of budmunchiamine C against other microorganism

| Organism | MIC | MBC |
|---|---|---|
| *Microsporum canis* | >0.0375% (375 ug/mL) | >0.0375% (375 ug/mL) |
| *Trichophyton mentagrophytes* | 0.001172% (11.7 ug/mL) | 0.001172% (11.7 ug/mL) |
| *Trichophyton rubrum* | 0.001172% (11.7 ug/mL) | 0.004688% (46.8 ug/mL) |
| *Propionibacterium acnes* | 0.0001953% (1.95 ug/mL) | 0.00078125% (7.8 ug/mL) |
| *Staphylococcus epidermis* | 0.003125% (31.25 ug/mL) | 0.003125% (31.25 ug/mL) |
| *Streptococcus pyogenes* | <0.00009765% (<0.97 ug/mL) | <0.000097656% (<0.97 ug/mL) |

Example 7

Analytical Method for Analysis of *Magnolia* Stem Bark Extracts

The *Magnolia* stem bark extracts were analyzed by RP-HPLC method by quantification of active marker compounds honokiol and magnolol. The extract was prepared as a methanol solution sonicated for approximately 10 minutes. The flask was cooled to room temperature and QS with extraction method; mixed well and filtered through a 0.45 um nylon syringe filter and 20 µl solutions were injected and analyzed. magnolol and honokiol content in *Magnolia* stem bark extracts were quantified by RP-HPLC method on an Agilent HPLC/PDA system with the C18 column (Phenomenex, USA). A binary purified water and acetonitrile solvent system was used for detection of magnolol and honokiol with isocratic elution of 77% acetonitrile in water for 18 min at a flow rate of 1 mL/min with a column temperature of 35° C. at a wavelength of 290 nm. The honokiol and magnolol content in the *Magnolia* stem bark Extract (FP072312-01) were determined as 51.2% and 47.2% respectively, with a total content of 98.4% in the extract.

The natural content of honokiol and magnolol in *Magnolia* bark were reported in a range of 2-11% and 0.3-4.6% respectively. The total content of honokiol and magnolol in the commercial *Magnolia* bark extract could be enriched and customized to a range of 1-99%.

Example 8

Anti-Microbial Activities of *Magnolia* Stem Bark Extracts

*Magnolia* bark with a common name houpu in Chinese is one of the popular traditional herbal medicines with a very wide range of applications. Many of the formulations with *Magnolia* bark are used in treating lung diseases such as including cough and asthma or intestinal infections and spasms, relieving abdominal swelling of various causes and edema. Essential oil was identified as the active constituents with two major marker compounds honokiol and magnolol. Modern researches have shown that *Magnolia* stem bark extract exhibited potent anti-microbial activities. Seven microorganisms were chosen to test the anti-microbial activity and *Magnolia*'s potential usage as anti-microbial agents including bacterial *Staphylococcus aureus*, *Escherichia coli*, and fungus strains *Microsporum canis*, *Trichophyton mentagrophytes*, *Trichophyton rubrum*, *A. brasiliensis* and *C. albicans*. MIC and MBC were determined following the standard protocol as described in example 6 with activity results in Table 6. Except anti-bacterial activity, *Magnolia* stem bark Extract also demonstrated d potent anti-fungal activity with a MIC value of 80 ug/mL against *C. albicans*.

TABLE 6

Anti-microbial activities of Magnolia stem bark Extract FP072312-01

| Organism/strain | MIC (ug/mL) | MBC (ug/mL) |
|---|---|---|
| *Staphylococcus aureus* | 80 | * |
| *Escherichia coli* | negative | negative |
| *Pseudomonas aeruginosa* | negative | negative |
| *Candida albicans* | 80 | * |
| *Aspergillus brasiliensis* | 400 | * |
| *Microsporum canis* | * | 118 |
| *Trichophyton mentagrophytes* | 59 | 59 |
| *Trichophyton rubrum* | 59 | 59 |

* Unable to be determined

Example 9

Anti-Fungal Activity of the Mixture of *Albizia* Seeds Extract and *Magnolia* Bark Extract In order to find composition effective against all five microorganisms required by category 2 preserve in USP chapter <51>, mainly targeting on boosting the anti-fungal activity, specifically against *C. albicans* and *A. brasiliensis*, the *Albizia amara* seeds extract and *Magnolia* barks extract were blended together to search for unexpected enhanced outcomes.

These two materials were formulated at different ratios by mixing the samples dissolved in methanol with desired amount and then dried in vacuum to get the mixture. By manufacture, the *Albizia amara* seeds extract and *Magnolia* barks extract could be directly mixed at the desired ratio to prepare the combination composition.

Compositions 1A:1M and 1A:3M, where A stands for *Albizia amara* seeds extract and M for *Magnolia* barks extract, yielded similar inhibitions with MIC at 30 ug/mL against *C. albicans*, relatively weaker activity against *A. brasiliensis* with MIC at 130 ug/m L. The third ingredient *Psoralea corylifolia* seeds extract (P) was added to the 1A: 6M compo at a ratio of 3P, however this three-ingredient formulation (1A:6M:3P) didn't show superior activity compared with two-ingredient compositions. Given the fact that the 1:1 ratio of the *Albizia amara* seeds extract and *Magnolia* barks extract composition (416-145-50) resulted in the best MIC against both *C. albicans* and *A. brasiliensis*. This composition was considered as the lead composition and was selected for further assessment in the anti-microbial effectiveness test following <USP51> chapter with details in Example 12.

TABLE 7

Anti-microbial activities of combinations against *C. albicans* and *A. brasiliensis*.

| Sample code | Composition | Candida albicans MIC (ug/mL) | Aspergillus brasiliensis MIC (ug/mL) |
|---|---|---|---|
| 416-145-50 | A:M = 1:1 | 30 | 130 |
| 416-145-75 | A:M = 1:3 | 30 | 130 |
| 416-145-M3 | A:M:P = 1:6:3 | 60 | 130 |

* A: *Albizia amara* seeds extract.
M: *Magnolia* barks extract.
P: *Psoralea corylifolia* seeds extract

Example 10

Evaluations of Synergy for the Compositions of Mixture of *Albizia* Seed Extracts and *Magnolia* Bark Extract In vitro antifungal combinations are commonly evaluated on the basis of the fractional inhibitory concentration (FIC) index, which represents the sum of the FIC of each substance tested. FIC is defined for each substance as (MIC of drug A in combination/MIC of drug A alone). The FIC index equation is based on the hypothesis that that a drug cannot interact with itself and therefore the effect of a self-drug combination will be always additive with FIC index at 1. The FIC index lower or higher than 1 indicates synergy or antagonism in terms of the interactions between two drugs combined. Considering the 2-fold drug dilution scheme, FIC index in the range of 0.5-4 was considered no interaction either additive or indifference for the drug combinations. Cutoff of 0.5 or less was suggested for defining synergy, while cutoff 4 or above was interpreted as antagonism (Farrar 1973; Huang 2013; Odds, 2003; Pankey, 2005).

The fractional inhibitory concentration (FIC) was calculated with the equation: FIC of drug A (FIC A)=MIC of drug A in combination/MIC of drug A alone, and FIC of drug B (FIC B)=MIC of drug B in combination/MIC of drug B alone]. The FIC Index (FICI), calculated as the sum of each FIC ($\Sigma$FIC). The FIC index for the combination study was calculated as shown in Table 8. The calculated index of 1A:1M and 1A:3M against *C. albicans* were 0.187 and 0.292. For *A. brasiliensis*, similar calculation leads to the FIC index at 0.293 and 0.309 for 1A:1M and 1A:3M respectively. The FCI index at 0.187 and 0.282 for the 1A:1M combination showed greater certainty as synergistic effect instead of additive. For 1A:3M combination, similar synergistic effect was observed against these two fungal strains with FIC index at 0.282 and 0.309. 1A:6M:3P combination had a weak synergistic effect against *C. albicans*, but no interaction effect against *A. brasiliensis*.

The anti-fungal activity of this combination study indicated the existence of synergy in formulating these two ingredients at a specific ratio. The combination of 1A:1M was found with boosted anti-fungal effects against both *C. albicans* and *A. brasiliensis*, which was classified as synergistic interaction based on the FIC index analysis with FIC index less than 0.5. The merit of putting the *Albizia amara* seeds extract and *Magnolia* barks extract together was confirmed by their unexpected enhanced anti-fungal activity against both *C. albicans* and *A. brasiliensis*.

TABLE 8

Unexpected synergistic anti-fungal activity of composition of *Albizia amara* seeds extract and *Magnolia* stem barks extract

| Sample code | Composition | Candida albicans MIC (ug/mL) | Candida albicans FIC index | Aspergillus brasiliensis MIC (ug/mL) | Aspergillus brasiliensis FIC index |
|---|---|---|---|---|---|
| A | | negative | | 500 | |
| M | | 80 | | 400 | |
| P | | negative | | 30 | |
| 416-145-50 | A:M = 1:1 | 30 | 0.188 | 130 | 0.293 |
| 416-145-75 | A:M = 1:3 | 30 | 0.282 | 130 | 0.309 |
| 416-145-M3 | A:M:P = 1:6:3 | 60 | 0.45 | 130 | 1.521 |

*A: *Albizia amara* seeds extract.
M: *Magnolia* barks extract.
P: *Psoralea corylifolia* seeds extract

Example 11

Figure 3:
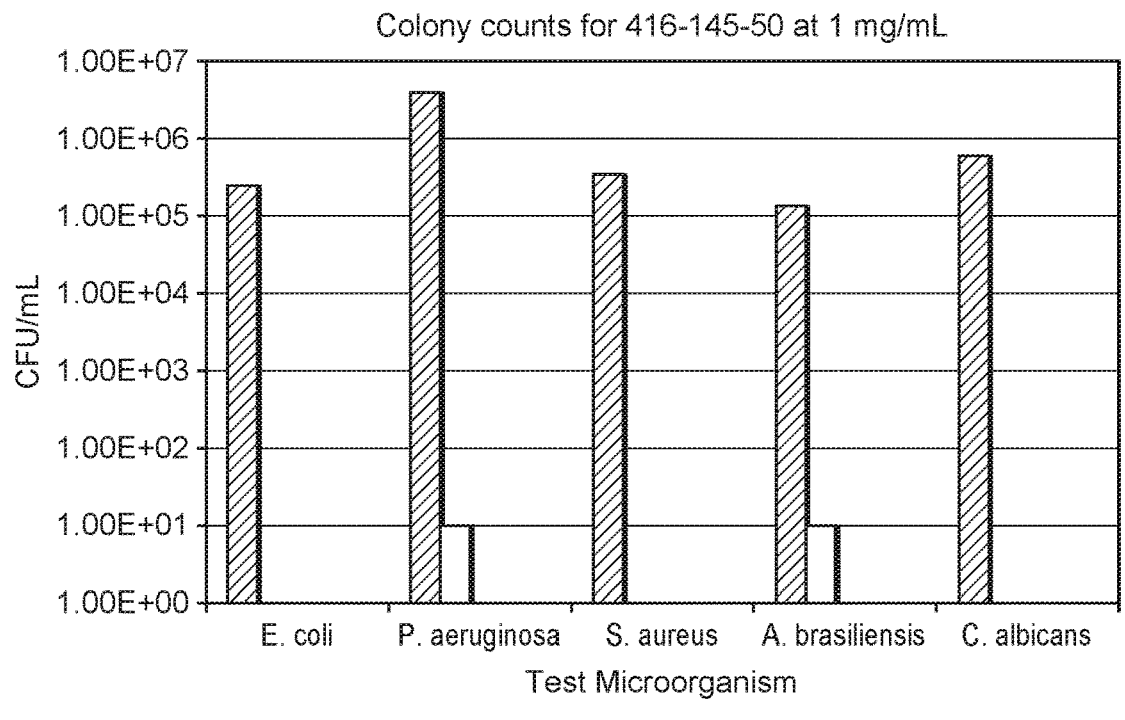

Effectiveness Test of Mixture of *Albizia* Seed Extract and *Magnolia* Bark Extract The antibacterial activity and efficacy of a contemplated preservative was evaluated following the USP <51> guideline. The USP <51> test method is a quantitative assessment of antimicrobial preservatives added to non-sterile dosage forms. The parameters used for this test are determined by the nature product and which of 4 categories it applies to. Typical contact times extend to 28 days with observations in remaining microbial content made in 7 day intervals. This test is traditionally accompanied by a neutralization validation assay to confirm the neutralization method employed is appropriate for the test substance and microorganism. Test substance 1A:1M combination (416-145-50) was dissolved in DMSO at a concentration of 1 mg/mL. The results are shown in FIG. 3. The test microorganisms *Staphylococcus aureus* (ATCC 6538), *Escherichia coli* (ATCC 8739), *Pseudomonas aeruginosa* (ATCC 9027), *Candida albicans* (ATCC 10231), *Aspergillus brasiliensis* (ATCC 16404) are prepared by growth in liquid or on agar culture medium. Microorganisms grown in liquid culture are centrifuged and washed prior to test. Suspensions of test microorganisms are standardized by dilution in a buffered saline solution. Test and control substances are dispensed, in similar known volumes, to sterile vessels. Independent volumes of Test and Control substances are inoculated with each test microorganism mixed and incubated. Control substances are immediately harvested and represent the concentration present at the start of the test, or time zero.

Incubated Test Substances are harvested at the conclusion of each contact time by chemical neutralization. The number of surviving microorganisms are assessed at 2, 7, 14, and 28 days and logarithmic reductions are calculated based on initial concentrations observed at time zero. The $Log_{10}$ Reduction was calculated as Log (B/A), where B=Number of viable test microorganisms in the control substances immediately after inoculation, and A=Number of viable test microorganisms in the test substances after the contact time. 416-145-50 significantly reduce the counts of *P. aeruginosa*, and *A. brasiliensis* with $Log_{10}$ reduction at 5.58 and 4.1 respectively and significantly, if not completely, eliminate *S. aureus*, *E. coli*, and *C. albicans* after 2 days, and no bacteria or fungi growth was observed after 7 days, 14 days, and 28 days against all five microorganisms. This study clearly demonstrated that the effectiveness of this composition 416-145-50 against *E. coli*, *P. aeruginosa*, *S. aureus*, *A. brasiliensis*, and *C. albicans* and meet the category 2 requirement which are no less than 2-$Log_{10}$ reduction from the initial count 14 days and no increase from the 14 day's count at day 28 for bacteria and no increase from the initial calculated count at 14 and 28 days for yeast and molds.

TABLE 9

Colony counts and Log reduction for 416-145-50 at 1 mg/mL

| Contact Time | DataDescription | Test Microorganism | | | | |
|---|---|---|---|---|---|---|
| | | *E. coli* 8739 | *P. aeruginosa* 9027 | *S. aureus* 6538 | *A. brasiliensis* 16404 | *C. albicans* 10231 |
| Time Zero | CFU/mL | 2.60E+05 | 3.80E+06 | 3.55E+05 | 1.27E+05 | 6.10E+05 |
| 2 Days | CFU/mL | <5.00E+00 | 1.00E+01 | <5.00E+00 | 1.00E+01 | <5.00E+00 |
| | $Log_{10}$ Reduction | >4.72 | 5.58 | >4.85 | 4.1 | >5.09 |
| 7 Days | CFU/mL | <5.00E+00 | <5.00E+00 | <5.00E+00 | <5.00E+00 | <5.00E+00 |
| | $Log_{10}$ Reduction | >4.72 | >5.88 | >4.85 | >4.40 | >5.09 |
| 14 Days | CFU/mL | <5.00E+00 | <5.00E+00 | <5.00E+00 | <5.00E+00 | <5.00E+00 |
| | $Log_{10}$ Reduction | >4.72 | >5.88 | >4.85 | >4.40 | >5.09 |
| 28 Days | CFU/mL | <5.00E+00 | <5.00E+00 | <5.00E+00 | <5.00E+00 | <5.00E+00 |
| | $Log_{10}$ Reduction | >4.72 | >5.88 | >4.85 | >4.40 | >5.09 |

Note:
The limit of detection for this assay is 5.00E+00 CFU/mL.
Samples with no microbial recovery are reported as <5.00E+00 in the chart.

Example 12

Figure 4:
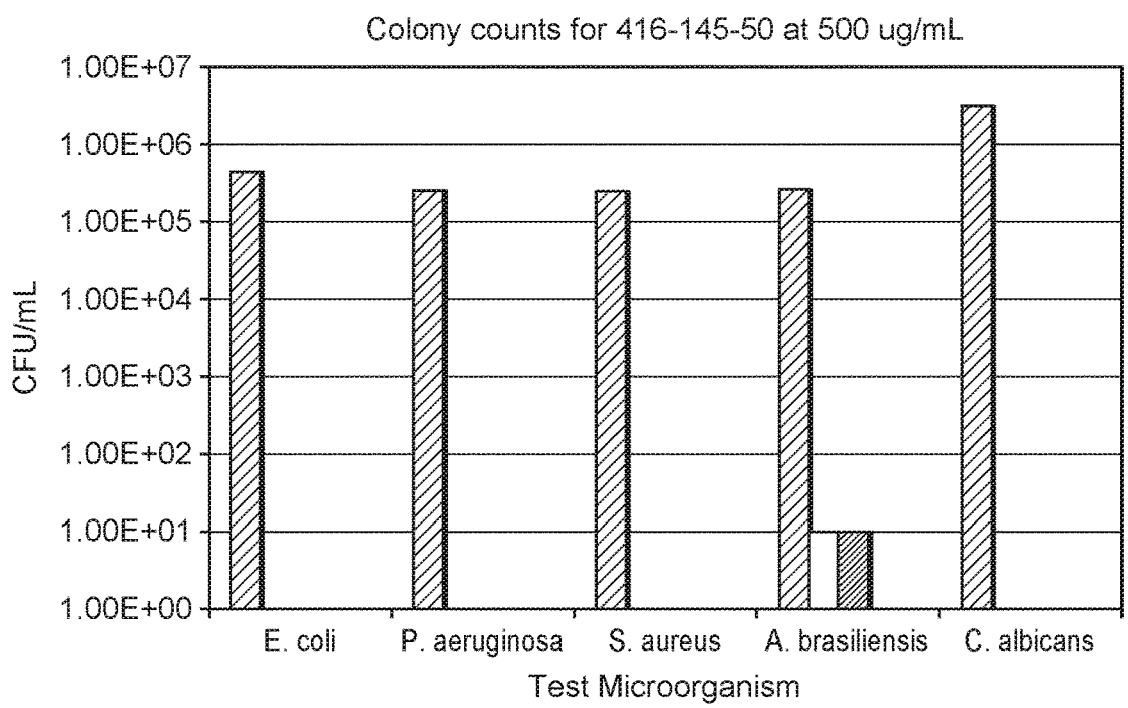

Effectiveness Test of Mixture of *Albizia* Seed Extract and *Magnolia* Bark Extract The antibacterial activity and efficacy of 1A:1M combination (416-145-50) was further evaluated following the USP <51> guideline as described in example 12 at a concentration of 0.5 mg/mL against *E. coli, P. aeruginosa, S. aureus, A. brasiliensis*, and *C. albicans*. The results are shown in FIG. 4. The number of surviving microorganisms are assessed at 48 hours, 7, 14, and 28 days and logarithmic reductions are calculated based on initial concentrations observed at time zero as shown in Table 10. This study clearly demonstrated that the effectiveness of this composition 416-145-50 at 0.05% against all five microorganism *E. coli, P. aeruginosa, S. aureus, A. brasiliensis*, and *C. albicans* and meet the category 2 requirement which are no less than 2-$Log_{10}$ reduction from the initial count 14 days and no increase from the 14 day's count at day 28 for bacteria and no increase from the initial calculated count at 14 and 28 days for yeast and molds.

TABLE 10

Colony counts and Log reduction for 416-145-50 at 500 µg/mL

| Contact Time | Data Description | Test Microorganism | | | | |
|---|---|---|---|---|---|---|
| | | *E. coli* 8739 | *P. aeruginosa* 9027 | *S. aureus* 6538 | *A. brasiliensis* 16404 | *C. albicans* 10231 |
| Time Zero | CFU/mL | 4.30E+05 | 2.40E+05 | 2.45E+05 | 2.50E+05 | 3.20E+06 |
| 2 Days | CFU/mL | <5.00E+00 | <5.00E+00 | <5.00E+00 | 1.00E+01 | <5.00E+00 |
| | $Log_{10}$ Reduction | >4.93 | >4.68 | >4.69 | 4.4 | >5.81 |
| 7 Days | CFU/mL | <5.00E+00 | <5.00E+00 | <5.00E+00 | 1.00E+01 | <5.00E+00 |
| | $Log_{10}$ Reduction | >4.93 | >4.68 | >4.69 | 4.4 | >5.81 |
| 14 Days | CFU/mL | <5.00E+00 | <5.00E+00 | <5.00E+00 | <5.00E+00 | <5.00E+00 |
| | $Log_{10}$ Reduction | >4.93 | >4.68 | >4.69 | >4.70 | >5.81 |
| 28 Days | CFU/mL | <5.00E+00 | <5.00E+00 | <5.00E+00 | <5.00E+00 | <5.00E+00 |
| | $Log_{10}$ Reduction | >4.93 | >4.68 | >4.69 | >4.70 | >5.81 |

Note:
The limit of detection for this assay is 5.00E+00 CFU/mL. Samples with no microbial recovery are reported as <5.00E+00 in the chart.

Example 13

Antimicrobial Activity of Mixture of *Albizia* Seed Extract and *Magnolia* Bark Extract Minimum Inhibitory Concentration against bacteria *S. aureus, P. aeruginosa*, and *E. coli*, were determined for 1A:1M combination of *Albizia amara* seeds extract and *Magnolia* bark extract. The Minimum Inhibitory Concentration Method (MIC) is carried out following the general microbiological protocol to measure the lowest level of an antimicrobial agent that can inhibit microbial proliferation in liquid as described in example 6 with activity results in Table 11. Potent antimicrobial activity against *Staphylococcus aureus* was found with MIC of 20 ug/mL. MIC of 1000 ug/mL was determined against both gram negative bacteria *Escherichia coli* and *Pseudomonas aeruginosa* for this *Albizia amara* seeds extract and *Magnolia* bark extract combination.

TABLE 11

Anti-microbial activities of 1A:1M combination (416-145-50)

| Organism/strain | MIC (ug/mL) |
| --- | --- |
| *Staphylococcus aureus* | 20 |
| *Escherichia coli* | 1000 |
| *Pseudomonas aeruginosa* | 1000 |

Example 14

Antimicrobial Activity of *Albizia amara* Seeds Extract Against *Escherichia coli* at PH=3

Minimum Inhibitory Concentration against gram negative bacterium *Escherichia coil* at acidic condition (PH=3) was determined for *Albizia amara* seeds extract (RN368-31-mix).

The Minimum Inhibitory Concentration Method (MIC) is carried out following the general microbiological protocol to measure the lowest level of an antimicrobial agent that can inhibit microbial proliferation in liquid. The test substance is dissolved in buffer solution at PH=3 with mixture of citric acid and sodium citrate in water, then prepared by several serial 1:1 dilutions in a 96-well microtiter plate, through Mueller-Hinton broth or other appropriate medium. All wells or tubes containing diluted test substances are inoculated with test microorganisms, individually, resulting in one additional and final dilution of the product in all test vessels. The microtiter plate is incubated for 18-24 hours. After the incubation period, observations are made to determine the minimum concentration (MIC) which is the lowest concentration of test substance in a well where no turbidity (indicative of test microorganism growth) is observed. The MIC was 125 ug/mL against *E. coli* for the *Albizia amara* seed extract at PH=3, slightly weaker activity compared to MIC at neural condition (62.5 ug/mL).

Example 15

Antifungal Activity of *Albizia amara* Seeds Extract and *Magnolia* Bark Extract Combination Against *Aspergillus brasiliensis* at PH=3

Minimum Inhibitory Concentration against *A. brasiliensis* at acidic condition (PH=3) was determined for the *Albizia amara* seeds extract *Magnolia* bark extract combination.

The Minimum Inhibitory Concentration Method (MIC) is carried out following the general microbiological protocol to measure the lowest level of an antimicrobial agent that can inhibit microbial proliferation in liquid. The test substance is dissolved in buffer solution at PH=3 with mixture of citric acid and sodium citrate in 20% DMSO/water, then further prepared by several serial 1:1 dilutions in a 96-well microtiter plate, through Mueller-Hinton broth or other appropriate medium. All wells or tubes containing diluted test substances are inoculated with test microorganisms, individually, resulting in one additional and final dilution of the product in all test vessels. The microtiter plate or test tubes are incubated for 18-24 hours. After the incubation period, observations are made to determine the minimum concentration (MIC) which is the lowest concentration of test substance in a well where no turbidity (indicative of test microorganism growth) is observed. The MIC was determined as 125 ug/mL for this 1A:1M combination at PH=3. The antifungal activity is improved for this 1A:1M combination at acidic condition compared to original MIC of 400 ug/mL.

Example 16

Formulation of Mixture of *Albizia* Seed Extract and *Magnolia* Bark Extract

1A:1M combination (B1-11202015) was further formulated with non-ionic o/w emulsion system at two concentrations 0.1% and 0.5% respectively. 3% (% by weight) 1,2-hexanediol was used as carrier solvent for B1-11202015 by weight in cream formulations with PH of the emulsion in a range of 6.0-6.5. B1-11202015 was completely dispersed in 3% 1,2 Hexanediol by weight at 50° C. before adding to the cream base. The cream base was prepared by mixing all ingredients at 70° C. until it is uniform and all solid materials have melted and mixed. The PH value of the cream base material will be adjusted to 6.0-6.5 after cooling down to 60° C. by adding 20% NaOH solution or 20% citric acid solution. The cream base was cool down to 50° C. before adding the 3% 1,2 Hexanediol and B1-11202105. The PH value of the formulated material will be further adjusted to the range of 6.0-6.5 if necessary. Two formulated samples were prepared with 0.5% 1A:1M combination (1940601) and 0.1% 1A:1M (1940602) in the same fashion.

Example 17

Figure 5:
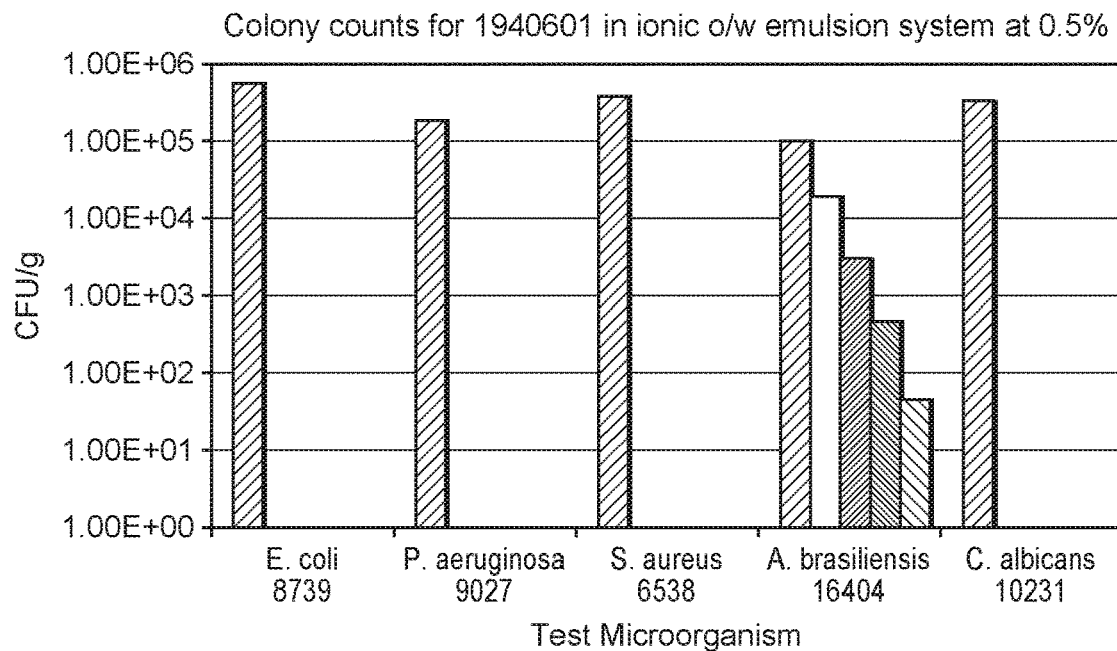
Figure 5:
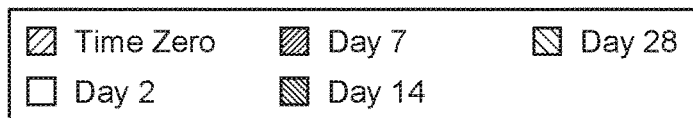

Effectiveness Test of Formulated *Albizia* Seed Extract and *Magnolia* Bark Extract Combination The antibacterial activity and efficacy of non-ionic o/w emulsion formulated 1A:1M combination at a concentration of 0.5% (1940601) was evaluated following the USP <51> guideline as described in Example 11 against *E. coli, P. aeruginosa, S. aureus, A. brasiliensis*, and *C. albicans*. The results are shown in FIG. 5. The number of surviving microorganisms is assessed at 2, 7, 14, and 28 days and logarithmic reductions are calculated based on initial concentrations observed at time zero as shown in Table 12. This study clearly demonstrated the effectiveness of this composition 1940601 at 0.5% against all three bacteria, *E. coli, P. aeruginosa, S. aureus*, and the yeast *C. albicans*, with no bacteria or fungi growth observed after 2 days, and extend to 7 days, 14 days, and 28 days. For *A. brasiliensis*, 1940601 showed relatively weaker inhibition with $Log_{10}$ reduction 0.73 and 1.53 at D2 and D7 respectively. It did reach 2-$LOG_{10}$ reduction at D14 (2.32) at D28 (3.32).

Figure 6:
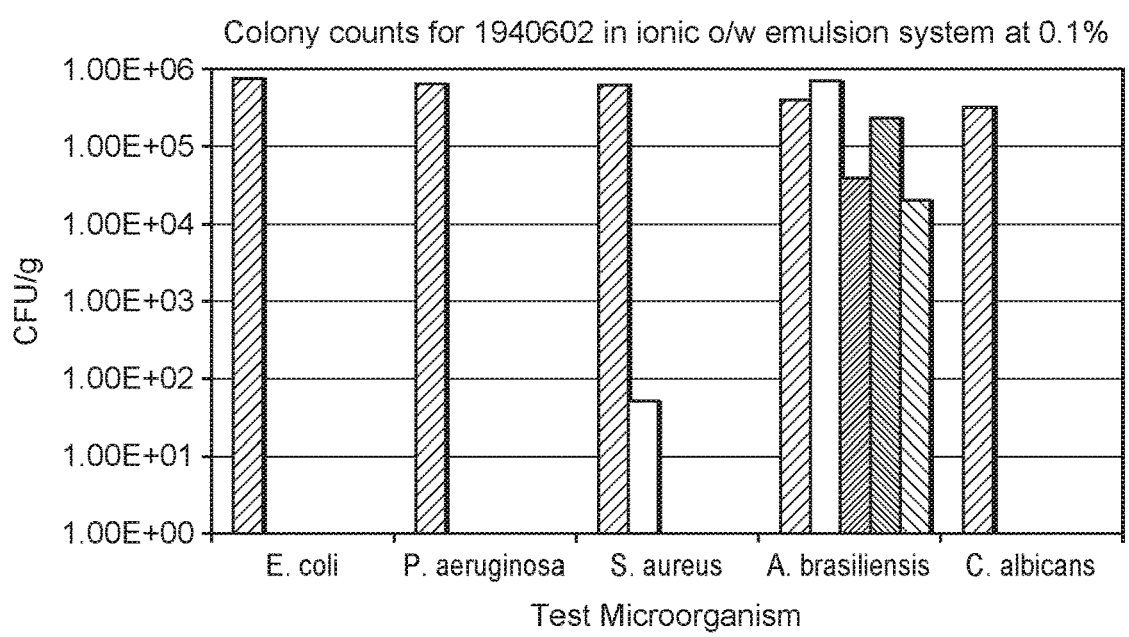
Figure 6:
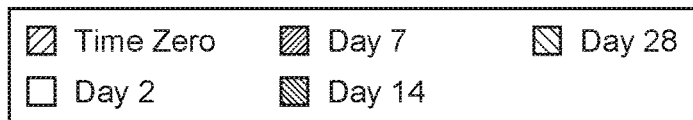

This study clearly demonstrated that the effectiveness of this composition 1940601 against all five strains E. coli, P. aeruginosa, S. aureus, A. brasiliensis, and C. albicans as category 2 products by passing USP51 criteria, which require no less than 2-$LOG_{10}$ reduction from the initial count at 14 days, and no increase from the 14 days count at 28 days for bacteria and no increase from the initial count at 14 and 28 days for yeast and mold.

nosa, S. aureus, A. brasiliensis, and C. albicans. The results are shown in FIG. 6. The number of surviving microorganisms is assessed at 2, 7, 14, and 28 days and logarithmic reductions are calculated based on initial concentrations observed at time zero as shown in Table 13.

This study demonstrated that this composition 1940602 at 0.1% eliminated E. coli, P. aeruginosa, S. aureus, and C. albicans starting Day 2. No growth was observed at all four contact time points D2, D7, D14 and D28. For A. brasiliensis, no inhibition was found at D2, with improvement

TABLE 12

Colony counts and Log reduction for 1940601 at 0.5% concentration

| | | Test Microorganism | | | | |
|---|---|---|---|---|---|---|
| Contact Time | Data Description | E. coli 8739 | P. aeruginosa 9027 | S. aureus 6538 | A. brasiliensis 16404 | C. albicans 10231 |
| Time Zero | CFU/mL | 5.83E+05 | 1.90E+05 | 3.71E+05 | 1.04E+05 | 3.30E+05 |
| 2 Days | CFU/mL | <5.00E+01 | <5.00E+01 | <5.00E+01 | 1.95E+04 | <5.00E+01 |
| | $Log_{10}$ Reduction | >4.03 | >3.58 | >3.87 | 0.73 | >3.82 |
| 7 Days | CFU/mL | <5.00E+01 | <5.00E+01 | <5.00E+01 | 3.05E+03 | <5.00E+01 |
| | $Log_{10}$ Reduction | >4.03 | >3.58 | >3.87 | 1.53 | >3.82 |
| 14 Days | CFU/mL | <5.00E+01 | <5.00E+01 | <5.00E+01 | 5.00E+02 | <5.00E+01 |
| | $Log_{10}$ Reduction | >4.03 | >3.58 | >3.87 | 2.32 | >3.82 |
| 28 Days | CFU/mL | <5.00E+01 | <5.00E+01 | <5.00E+01 | 5.00E+01 | <5.00E+01 |
| | $Log_{10}$ Reduction | >4.03 | >3.58 | >3.87 | 3.32 | >3.82 |

Note:
The limit of detection for this assay was 50 CFU/g. Values observed below the limit of detection are noted as <5.00E+01 in the table.

Example 18

Effectiveness Test of Formulated *Albizia* Seed Extract and *Magnolia* Bark Extract Combination The antibacterial activity and efficacy of 1A:1M combination formulated with non-ionic o/w emulsion system (1940602) was further evaluated at 0.1% concentration in the challenge testing following USP <51> guideline as described in Example 11 against 5 strains E. coli, P. aerugiafter D2. $Log_{10}$ reductions are 1.02, 0.23 and 1.33 at D7, D14, and D28 respectively. This study clearly showed that this composition 1940602 was effective against E. coli, P. aeruginosa, S. aureus, A. brasiliensis, and C. albicans and qualified 1940602 as category 2 products by passing USP51 criteria, which require no less than 2-$LOG_{10}$ reduction from the initial count at 14 days, and no increase from the 14 day's count at 28 days for bacteria and no increase from the initial count at 14 and 28 days for yeast and mold.

TABLE 13

Colony counts and Log reduction for 1940602 at 0.1% concentration

| | | Test Microorganism | | | | |
|---|---|---|---|---|---|---|
| Contact Time | Data Description | E. coli 8739 | P. aeruginosa 9027 | S. aureus 6538 | A. brasiliensis 16404 | C. albicans 10231 |
| Time Zero | CFU/mL | 8.55E+05 | 6.70E+05 | 6.45E+05 | 4.35E+05 | 3.40E+05 |
| 2 Days | CFU/mL | <5.00E+01 | <5.00E+01 | 5.00E+01 | 7.00E+05 | <5.00E+01 |
| | $Log_{10}$ Reduction | >4.23 | >4.13 | 4.11 | None | >3.83 |
| 7 Days | CFU/mL | <5.00E+01 | <5.00E+01 | <5.00E+01 | 4.20E+04 | <5.00E+01 |
| | $Log_{10}$ Reduction | >4.23 | >4.13 | >4.11 | 1.02 | >3.83 |
| 14 Days | CFU/mL | <5.00E+01 | <5.00E+01 | <5.00E+01 | 2.55E+05 | <5.00E+01 |
| | $Log_{10}$ Reduction | >4.23 | >4.13 | >4.11 | 0.23 | >3.83 |
| 28 Days | CFU/mL | <5.00E+01 | <5.00E+01 | <5.00E+01 | 2.55E+04 | <5.00E+01 |
| | $Log_{10}$ Reduction | >4.23 | >4.13 | >4.11 | 1.33 | >3.83 |

Note:
The limit of detection for this assay was 50 CFU/g. Values observed below the limit of detection are noted as <5.00E+01 in the table.

Example 19

Effectiveness Test of Mixture of *Albizia* Seeds Extract and *Magnolia* Bark Extract The antibacterial activity and efficacy of 1A:1M combination (416-145-50) was formulated with a non-ionic o/w emulsion system at a level of 5% and further evaluated following the USP <51> guideline as described in Example 12 against *A. brasiliensis* only. The number of surviving microorganisms is assessed at 48 hours, 7, 14 days as shown in table 12. This study clearly demonstrated the effectiveness of this composition 416-145-50 at 5% against *A. brasiliensis* and no growth of detectable colonies of this microorganism was observed after 48 hours.

TABLE 14

Colony counts and Log reduction for 5% 416-145-50 in a non-ionic o/w emulsion system

| Contact Time | Data Description | Test Microorganism *A. brasiliensis* 16404 |
|---|---|---|
| Time Zero | CFU/mL | 9.00E+05 |
| 48 Hours | CFU/mL | <5.00E+01 |
| Day 7 | CFU/mL | <5.00E+01 |
| Day 14 | CFU/mL | <5.00E+01 |

Note:
The limit of detection for this assay is 5.00E+00 CFU/mL. Samples with no microbial recovery are reported as <5.00E+00 in the chart.

REFERENCES

1. Assis T S, Almeida R N, da-Cunha E V L, Medeiros I A, A. M. Lima, Souza M F V, Silva M S, Braz-Filho R, and Barbosa-Filho J M. Two new macrocyclic alkaloids from Alibizia inopinata. Acta Farm. Bonaerense. 1999, 18 (4): 271-275.
2. Bang K. H., Kim Y. K., Min B. S., et al. Antifungal activity of magnolol and honokiol. *Archives of Pharmacal Research*. 2000; 23:46-49.
3. Dixit K A, Misra L N. Macrocyclic budmunchiamine alkaloids from *Albizia lebbek*. J. Nat. Prod. 1997, 60 (10): 1036-1037.
4. Farrar W E Jr, Newsome J K. Mechanism of synergistic effects of beta-lactam antibiotic combinations on gram-negative bacilli. Antimicrob Agents Chemother. 1973; 4(2):109-14.
5. Fried L. E., Arbiser J. L. Honokiol, a multifunctional antiangiogenic and antitumor agent. Antioxidants & Redox Signaling. 2009; 11(5):1139-1148.
6. Geyid A, Abebe D, Debella A, Makonnen Z, Aberra F, Teka F, Kebede T, Urga K, Yersaw K, Beza T, Mariam B H, Guta M. Screening of some medicinal plants of Ethiopia for their anti-microbial properties and chemical profiles. J. Ethnopharmacology. 2005; 97:421-427.
7. Ho K Y, Tsai C C, Chen C P, Huang J S, Lin C C. Antimicrobial activity of honokiol and magnolol isolated from *Magnolia officinalis*. Phytotherapy Research. 2001; 15:139-141.
8. Hwang J H, Choi H, Woo E R, Lee D G. Antibacterial effect of amentoflavone and its synergistic effect with antibiotics. J Microbiol Biotechnol. 2013; 23(7):953-8.
9. Kim S Y, Kim J, Jeong S I, Jahng K Y, Yu K Y. Antimicrobial Effects and Resistant Regulation of Magnolol and Honokiol on Methicillin-Resistant *Staphylococcus aureus*. Biomed Res Int. 2015; 2015:283630. doi: 10.1155/2015/283630. Epub 2015 Aug. 19.
10. Mar W, Tan G T, Cordell G A, Pezzuto J M, Jurcic K, Offermann F, Redl K, Steinke B, Wagner H. Biological activity of novel macrocyclic alkaloids (budmunchiamines) from *Albizia amara* detected on the basis of interaction with DNA. J Nat Prod. 1991; 54(6):1531-42.
11. Misra L N; Dixit, A K; Wagnert H. N-demethyl budmunchiamines from *Albizzia lebbek* seeds. Phytochemistry 1995: 39(1): 247-249.
12. Odds F C. 2003. Synergy, antagonism, and what the checkerboard puts between them. J. Antimicrob. Chemother. 52: 1.
13. Ovenden S P B, Cao S, Leong C, Flotow H, Gupta M P, Buss A D., and Butler M S. Spermine alkaloids from *Albizia adinocephala* with activity against Plasmodium falciparum, plasmepsin II. Phytochemistry 2002, 60 (2): 175-177.
14. Pankey G A, Ashcraft D S. In vitro synergy of ciprofloxacin and gatifloxacin against ciprofloxacin-resistant *Pseudomonas aeruginosa*. Antimicrob. Agents Chemother. 2005; 49: 2959-2964
15. Park J., Lee J., Jung E., et al. In vitro antibacterial and anti-inflammatory effects of honokiol and magnolol against *Propionibacterium* sp. European Journal of Pharmacology. 2004; 496:189-195.
16. Pezzutoa J M, Mar W, Lin L Z, Cordell G A, Neszmélyib A, Wagnerc H. Budmunchiamines D-I from *Albizia amara*. Phytochemistry. 1992; 31(5): 1795-1800.
17. Samoylenko V, Jacob M R, Khan S I, Zhao J, Tekwani B L, Midiwo J O, Walker L A, and Muhammad I. Antimicrobial, antiparasitic and cytotoxic spermine alkaloids from *Albizia schimperiana*. Nat. Prod. Commun. 2009, 4 (6): 791-796.
18. Thippeswamy S, Mohana D C, Abhishek R U, Manjunath K. Evaluation of some pharmacological activities of Budmunchiamine-A isolated from *Albizia amara*. Braz J Microbiol. 2015; 46(1):139-43.

Thus, specific embodiments and methods of compounds and compositions useful for preservatives and antimicrobial agents, including stereoisomers, pharmaceutically or nutraceutically acceptable salts, tautomers, glycosides and prodrugs of the disclosed compounds, along with related methods of improving and maintaining liver health have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The invention claimed is:

1. A composition, comprising: a mixture of at least one *Albizia* extract and at least one *Magnolia* extract, wherein the at least one *Albizia* extract is enriched for one or more macrocyclic alkaloids, wherein the at least one *Magnolia* extract is enriched for one or more lignans, and wherein the at least one *Albizia* extract and the at least one *Magnolia* extract are blended in a weight ratio ranging from 1:1 to 1:3.

2. A food, cosmetic, nutraceutical or pharmaceutical that comprises the composition of claim 1, wherein the composition is a preservative.

3. The composition of claim 2, wherein the composition is present in the food, cosmetic, nutraceutical or pharmaceutical in a range from about 0.001% to about 10% by weight of the total weight of the food, cosmetic, nutraceutical or pharmaceutical.

4. The composition of claim 3, wherein the composition is present in the food, cosmetic, nutraceutical or pharmaceutical in a range from about 0.01% to about 5% by weight of the total weight of the food, cosmetic, nutraceutical or pharmaceutical.

5. The composition of claim 1, wherein the *Albizia* extract and the *Magnolia* extract are blended in a weight ratio at 1:1.

6. The composition of claim 1, wherein the *Albizia* extract comprises about 0.01% to 99.9% of macrocyclic alkaloids.

7. The composition of claim 1, wherein *Magnolia* extract comprises about 0.01% to 99.9% of diphenol lignans.

8. The composition of claim 1, wherein the *Albizia* is selected from *Albizia schimperiana, Albizia lebbek, Albizia gummifera, Albizzia inopinata, Albizia saman (Samanea saman=Pithecolobium saman), Albizia adianthifolia, Albizia adinocephala, Albizia anthelmintics, Albizia antunesiana, Albizia chevalieri, Albizia corniculata, Albizia crassiramea, Albizia duclouxii, Albizia glabra, Albizia julibrissin, Albizia kalkora, Albizia lebbekoides, Albizia myriophylla, Albizia nigricans, Albizia odoratissima, Albizia peterisana, Albizia poilanei, Albizia procera, Albizia tanganyicensis, Albizia vialeana pierre, Albizia zygia, Aphelandra fuscopunctata, Ephedra* spp., *Verbascum pseudonobile, Incarvillea sinensis, Verbascum phoenicum, Verbascum nigrum, Clerodendrum buchneri, Aphelandra squarrosa* or a combination thereof.

9. The composition of claim 1, wherein the at least one enriched *Albizia* extract is extracted from *Albizia* plants with water, ethanol, methanol, alcohol and water-mixed solvents, or by supercritical fluid.

10. The composition of claim 1, wherein the alkaloids isolated from the at least one *Albizia* extract comprise, Felipealbizine A, Felipealbizine B, 6'-Hydroxybudmunchiamine C, Pithecolobine, Protomethine, Verbamethine, Verbametrine, Isoverbametrine, Isoverbamethine, Verbamekrine, Isoverbamekrine, Verbascine, Verbacine, Verbasitrine, Verballocine, Isoverbasitrine, Verballoscenine, Isoverbasikrine, N1-(Z)-p-Methoxycinnamoylbuchnerine, Buchnerine, Verbamedine, Verbascenine, Verbascenine, Isoverbamedine, Schweinine, Prelandrine, Incasine B', Incasine B or a combination thereof.

11. The composition of claim 1, wherein the at least one enriched *Magnolia* extract is extracted from *Magnolia* plants with water, ethanol, methanol, alcohol and water mixed solvents, or by supercritical fluid.

12. The composition of claim 1, wherein the *Magnolia* comprises—*Magnolia acuminate, Magnolia biondii, Magnolia coco, Magnolia denudate, Magnolia fargesii, Magnolia garrettii, Magnolia grandiflora, Magnolia henryi, Magnolia liliflora, Magnolia kachirachirai, Magnolia kobus, Magnolia obovata, Magnolia praecocissima, Magnolia pterocarpa, Magnolia pyramidata, Magnolia rostrate, Magnolia salicifolia, Magnolia sieboldii, Magnolia soulangeana, Magnolia stellate, Magnolia virginiana,* prod. of degradation of birch lignin, *Acanthus ebracteatus, Aptosimum spinescens, Aralia bipinnata, Araucaria angustifolia, Araucaria araucana, Artemisia absinthium, Haplophyllum acutifolium, Haplophyllum perforatum, Liriodendron tulipifera, Krameria cystisoides, Perilla frutescens, Lawsonia inermis Myristica fragrans* (nutmeg), *Parakmeria yunnanensis* (preferred genus name *Magnolia*), *Persea japonica, Piper futokadsura, Piper wightii, Rollinia mucosa, Sassafras randaiense, Scrophularia albida-colchica, Stellera chamaejasme, Syringa velutina, Syzygium cumini, Talauma gloriensis, Virola elongate, Urbanodendron verrucosum, Wikstroemia sikokiana* or a combination thereof.

13. The composition of claim 1, wherein the lignans isolated from the at least one *Magnolia* extract comprise Biondinin A, 2,3-Bis(4-hydroxy-3-methoxyphenyl)-2-propenal, Denudadione C, Clovanemagnolol, 8-[2-Hydroxy-5-(2-propenyl)phenyl]-6-(2-propenyl)-2H-1-benzopyran-2-one, Denudanolide C, Denudanolide D, Denudanolide B, Denudanolide A, Denudatin A, Denudatin B; (+)-form, 4-Hydroxy-6'-methoxy-3,3'-biligna-7,7'-diene-9,9'-dial, 4'-Methoxymagndialdehyde, 5,5'-Di-2-propenyl-[1,1'-biphenyl]-2,2'-diol, 2,2'-Bichavicol, FEMA 4559, 5,5'-Diallyl-2,2'-dihydroxybiphenyl, Bornylmagnolol, 5,5'-Diallyl-2-(3-methyl-2-butenyloxy)biphenyl-2'-ol, 5,5'-Diallyl-2-(allyloxy)biphenyl-2'-ol, 3',5-Diallyl-2,4'-dihydroxybiphenyl, 3',5-Di-2-propenyl-2,4'-biphenyldiol, 5-Allyl-3'-(1-propenyl)biphenyl-2,4'-diol, 3'-(1-Propenyl)-5-(2-propenyl)-2,4'-biphenyldiol, 3',5-Diallyl-2-hydroxy-4'-methoxybiphenyl, 4'-O-Methylhonokiol, 2-Hydroxy-4'-methoxy-3',5-di-2-propenylbiphenyl, 4,4'-Diallyl-2,3'-dihydroxydiphenyl ether, 2-[3-Hydroxy-4-(2-propenyl)phenoxy]-5-(2-propenyl)phenol, 2-Hydroxy-3-methoxy-4',5-di-2-propenyldiphenyl ether, 4',5-Diallyl-2-hydroxy-3-methoxydiphenyl ether, 2-Methoxy-4-(2-propenyl)-6-[4-(2-propenyl)phenoxy]phenol, Fargesin, Methyl pluviatilol, 3,4-Dimethoxy-3',4'-methylenedioxy-7,9':7',9-diepoxylignan, Kobusin, Desmethoxyaschantin, O-Methylpiperitol, Spinescin, (+)-Fargesin, Planinin, Methylpluviatilol, Parakmerin A, 6-Allyl-7-(3,4-dimethoxyphenyl)-2,3-dimethoxy-8-methyltricyclo[4.2.0.02,8]oct-3-en-5-one, Magnosalin, Dipiperitylmagnolol, Kachirachirol B, Acuminatin, Licarin D, Eudeshonokiol A, Eudesmagnolol, Eudesmin; (+)-formm, (+)-Epieudesmin, (−)-Epieudesmin, Kachirachirol A, Eupomatenoid 13, Fargesiphenol B, Fargesiphenol C, Fargesone A, Fargesone B, 4,5-Dimethoxy-3',4'-methylenedioxy-2,7'-dioxo-5,8'-ligna-3,6,8-triene, 4-(1,3-Benzodioxol-5-yl)-2,3,4,5-tetrahydro-7-methoxy-5-methyl-8H-2,5a-methano-1-benzoxepin-8-one, Garrettilignan A, Garrettilignan B, Tetrahydro-4-(3-hydroxy-4,5-dimethoxyphenyl)-1H,3H-furo[3,4-c]furan-1-one, Kachiranol, 7',9-Dihydroxy-3,3',4,4',5-pentamethoxy-7,9'-epoxylignan, Magnone B, 3,3',4,4',5,9-Hexamethoxy-7,9'-epoxylignan-7'-one, Magnolenin C, 3',4,7,9,9'-Pentahydroxy-3,5'-dimethoxy-8,4'-oxyneolignan, 3,3'-Dimethoxy-4,5:4',5'-bis(methylenedioxy)pyramidatin, 3'-Hydroxy-3,4,4',5,5'-pentamethoxypyramidatin, Pyramidatin B, 3,3',4',5'-Tetramethoxy-4,5-methylenedioxypyramidatin, 3,3',4,4',5,5'-Hexamethoxypyramidatin, Pyramidatin C, Pyramidatin, Pyramidatin D, 3-Hydroxy-3',4,4',5,5'-pentamethoxypyramidatin, Pyramidatin A, 3-Hydroxy-3',4,5-trimethoxy-4',5'-methylenedioxypyramidatin, Pyramidatin F, Pyramidatin G, Pyramidatin H, Pyramidatin E, 5'-Hydroxy-3,3',4,4',5-pentamethoxypyramidatin, Magnoshinin, 2',3,4,4',5,6-Hexamethoxy-2,7'-cyclolign-7-ene, Acanthoside B, Eleutheroside E1, 3-Hydroxy-3',4,4',5,5'-pentamethoxy-7,9':7',9-diepoxylignan, (+)-Episyringaresinol, Lirioresinol A, Symplicosigenol, Kobusinol B, Fargesol, 9-O-Acetylfargesol, Magnolone, Biondinin B, Biondinin E, Magnone A, 7,9,9'-Trihydroxy-3,3',4-trimethoxy-8,4'-oxyneolignan, erythro-form, threo-form, Magnovatin A, Magnovatin B, Oleiferin C, 3,4:3',4'-Bis(methylendioxy)-7-lignanol, 7-Hydroxy-3,4:3',4'-bis(methylenedioxy)lignan, Liliflodione, Denudadione B, Denudadione A, Liliflol A, Liliflol B, Denudatone, 3-[2',6-Dihydroxy-5'-(2-propenyl) [1,1'-biphenyl-3-yl]]-2-propenal, Randainal, Magnaldehyde B, Magnaldehyde C, 6'-O-Methylmagnaldehyde B, 4-Deoxy-6-methoxymagnaldehyde A, 4-Methoxymagnaldehyde B (incorr.), 2',6-Dihydroxy-5'-(2-propenyl) [1,1'-biphenyl]-3-carboxaldehyde, 5-Allyl-5'-formyl-2,2'-dihydroxybiphenyl, Magnaldehyde E, 6-O-Methylmagnaldehyde E, 9-Hydroxy-3,3',4,4',5-pentamethoxy-7,9'-epoxylign-7'-ene, 9,9'-Dihydroxy-3,3',4,4',5-pentamethoxy-2,7'-cyclolign-7-ene, Magnolianin, Magnolignan I, Magnolignan B, Magnolignan A, Magnolignan D, Magnolignan C 6'-glucoside, Magnolignan C, Magnolignan E, Magnolignan F, Magnolignan G, Magnolignan H, 2-[4-Hydroxy-3-(2-propenyl)phenyl]-2,5-cyclohexadiene-1,4-dione, 2-(3-Allyl-4-hydroxyphenyl)-1, 4-benzoquinone, Magnosalicin; (7RS,7'SR,8RS,8'RS)-form, Magnostellin B, Magnostellin B; 7,9-Diepimer, 5-methoxy,5-[2-Hydroxy-5-(2-propenyl)phenyl]-2-methylbenzofuran, 3-Hydroxy-3',4,4',5-tetramethoxy-7,9',7',9-diepoxylignan, 3-De-O-methylmagnolin, Magnolin, 3-O-Demethylaschantin, Demethylaschantin, 3-Hydroxy-4,5-dimethoxy-3',4'-methylenedioxy-7,9':7',9-diepoxylignan, 5'-Hydroxy-4'-O-methylpiperitol, Epimagnolin A, 7'-Hydroxy-3,3',4,4'-tetramethoxy-7,9'-epoxylignan, Magnostellin A, Kobusinol A, 4,7'-Dihydroxy-3,3',4'-trimethoxy-7,9'-epoxylignan, 4',5,9-Trihydroxy-3,3'-dimethoxy-7,9'-epoxylignan, Fargesiphenol A, Liliflone, Monoterpenylmagnolol, Piperitylhonokiol, Monoterpenylhonokiol, Saulangianin I, Sesamin; (–)-form, Syringinoside, Syringin 4"-glucoside, 3,3',4,5'-Tetramethoxy-7,9':7',9-diepoxylignan, 3',5'-Dimethoxy-3,4-methylenedioxy-7,9':7',9-diepoxylignan, Galgravin, 2,2'-Dihydroxy-3-methoxy-5,5'-di-2-propenylbiphenyl, 3-Methoxymagnolol, 5,5'-Diallyl-2,2'-dihydroxy-3-methoxybiphenyl or a combination thereof.

14. The composition of claim 1, wherein the composition comprises:
- a mixture of at least one *Albizia* extract from a plant material or other source, and at least one *Magnolia* extract from a plant material or another source,
- wherein the at least one *Albizia* extract has an increase in an amount or an activity of one or more macrocyclic alkaloids as compared to the amount or the activity of the one or more macrocyclic alkaloids in the plant material or other source of the at least one *Albizia* extract, and
- wherein the at least one *Magnolia* extract has an increase in an amount or an activity of one or more lignans as compared to the amount or the activity of the one or more lignans in the plant material or other source of the at least one *Magnolia* extract.

15. The composition of claim 14, wherein the plant material or other source comprises stems, stem barks, trunks, trunk barks, twigs, tubers, roots, root barks, young shoots, seeds, rhizomes, flowers and other reproductive organs, tissue cultures and stem cell cultures, leaves and other aerial parts or a combination thereof.

16. The composition of claim 1, wherein the composition additionally comprises at least one known antimicrobial ingredients, wherein the ingredients comprise plant powder or plant extract of *Psoralea corylifolia*, Curcumin, Eugenol, *Alpinia galganga, coptidis, Azadirachta indica, Propolis*, clove oil, *Sophora flavescens, Areca catechu, Glycyrrhiza glabra l., Thuja plicata*, Cortex *phellodendri, Rheum* palate, *Alpinia officinarum, Curcuma longa, Broussonetia papyriferra, Viburnum cotinifolium, Euphorbia hirta linn, Vitex negundo*, or a combination thereof.

17. The composition of claim 1, wherein the composition additionally comprises at least one known antimicrobial ingredients, wherein the ingredients comprise calcium propionate, sodium benzoate, sodium nitrate, sodium nitrite, potassium sorbate, benzoic acid, salicylic acid, sorbic acid, alcohol, penoxyethanol, 1, 2-diol alcohol (1,2 propanediol, 1,2 butanediol, 1,2 pentanediol, 1,2-hexanediol,),1, 3-diol alcohol (1,3 propanediol, 1,3 butanediol, 1,3 pentaneidol, 1,3-hexanediol), 1,5 pentanediol, benzakonium chloride, parabens, sulfites (sulfur dioxide, sodium bisulfite, potassium hydrogen sulfite, etc.) and disodium EDTA, and BHT (butylated hydroxy toluene) and BHA (butylated hydroxyl) .anisole), formaldehyde (usually in solution), glutaraldehyde (kills insects), and methylchloroisothiazolinone.

18. The composition of claim 1, wherein the composition further comprises a pharmaceutically or nutraceutically acceptable carrier, diluent, or excipient, wherein the pharmaceutical or nutraceutical formulation comprises from about 0.001 weight percent (wt %) to about 10 wt % of active ingredients of the extract mixture.

19. The composition of claim 1, wherein the composition is formulated as a powder, granule, liquid, tincture, sashay, ready to drink shot, or lozenge, cosmetic cream, gel, lotion, shampoo, hire conditioner, body rinse, body lotion, hire color agent, skin color agent, eye color agent, lip bum, perfume, toothpaste, mouth washing, fruit juice, aloe juice, yogurt, foods, soft drink, beverage, processed fruits, cheese products, wine, gem, peanut butter, RTD, protein bar, or a snack bar.

\* \* \* \* \*